(12) United States Patent
Kodama et al.

(10) Patent No.: US 11,957,306 B2
(45) Date of Patent: Apr. 16, 2024

(54) DISTAL END FRAME OF ENDOSCOPE, DISTAL END UNIT, AND ENDOSCOPE

(71) Applicant: OLYMPUS CORPORATION, Tokyo (JP)

(72) Inventors: Daichi Kodama, Hachioji (JP); Tomokazu Yamashita, Ibaraki (JP); Takuro Horibe, Funabashi (JP); Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 470 days.

(21) Appl. No.: 17/475,925

(22) Filed: Sep. 15, 2021

(65) Prior Publication Data

US 2021/0401267 A1    Dec. 30, 2021

Related U.S. Application Data

(63) Continuation of application No. PCT/JP2019/011113, filed on Mar. 18, 2019.

(51) Int. Cl.
*A61B 1/00* (2006.01)
(52) U.S. Cl.
CPC ...... *A61B 1/00114* (2013.01); *A61B 1/00097* (2022.02); *A61B 1/00124* (2013.01)
(58) Field of Classification Search
CPC ............ A61B 1/00114; A61B 1/00097; A61B 1/00124; A61B 1/0008; A61B 1/0096;
(Continued)

(56) References Cited

U.S. PATENT DOCUMENTS 5,569,157 A    10/1996  Nakazawa et al.
2017/0127915 A1*  5/2017  Viebach ................. A61B 1/018

FOREIGN PATENT DOCUMENTS

CN    106061350 A    10/2016
JP    S60-66223 A    4/1985
(Continued)

OTHER PUBLICATIONS

International Search Report dated Jun. 11, 2019 received in PCT/JP2019/011113.
English abstract only of EP 2 596 738 A1.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

A distal end frame includes: a first distal end frame member that includes a resin molded product which constitutes a molded interconnect device; a housing chamber that is provided on a distal end side of the first distal end frame member, and is formed of a recessed portion a distal end and one side of which are opened; a second distal end frame member that is composed of the resin molded product constituting the molded interconnect device, and is configured to close the one side of the housing chamber; a signal pattern that is the metal pattern formed in a region including a first joining surface which is a joining surface with the second distal end frame member, on a surface of the first distal end frame member; and a solder material which is configured to join the first distal end frame member and the second distal end frame member.

10 Claims, 24 Drawing Sheets

(58) Field of Classification Search
CPC ....... A61B 1/05; A61B 1/00101; A61B 1/053; A61B 1/0011
USPC ........................................ 600/153, 175, 176
See application file for complete search history.

(56) References Cited

FOREIGN PATENT DOCUMENTS

| | | | |
|---|---|---|---|
| JP | 63-220838 | A | 9/1988 |
| JP | H06-315458 | A | 11/1994 |
| JP | 2001-136421 | A | 5/2001 |
| JP | 2009-201762 | A | 9/2009 |
| JP | 2010-035755 | A | 2/2010 |
| JP | 2011-240053 | A | 12/2011 |
| JP | 2012-064883 | A | 3/2012 |
| JP | 5139597 | B2 | 2/2013 |
| JP | 2015-229059 | A | 12/2015 |
| JP | 2017-505154 | A | 2/2017 |
| JP | 2017-113417 | A | 6/2017 |
| WO | 2012/032837 | A1 | 3/2012 |
| WO | 2015/082328 | A1 | 6/2015 |
| WO | 2018/084730 | A1 | 5/2018 |

* cited by examiner

DISTAL END FRAME OF ENDOSCOPE, DISTAL END UNIT, AND ENDOSCOPE

CROSS REFERENCE TO RELATED APPLICATION

This application is a continuation application of PCT/JP2019/011113 filed on Mar. 18, 2019, the entire contents of which are incorporated herein by this reference.

BACKGROUND OF THE INVENTION

1. Field of the Invention

The present invention relates to: a distal end frame of an endoscope provided with an image pickup unit inside the distal end frame; a distal end unit; and an endoscope.

2. Description of the Related Art

Conventionally, in order to observe a site where direct visual observation is difficult, such as an internal part of a living body or a structural object, an endoscope which is formed to be introduced from an outside toward an inside of the living body or the structural object and has such a structure as to be capable of forming an optical image or picking up the optical image has been widely used in the medical field or the industrial field.

In such an endoscope, a distal end portion provided at a distal end of an insertion portion is mainly composed of a distal end unit in which various functional components are provided on a hard distal end frame. As a distal end frame of such a distal end unit, a distal end frame using a technology of molded interconnect devices (MIDs) has been proposed in recent years. For example, in International Publication WO 2015/082328, an endoscope head (distal end unit of endoscope) is disclosed, which includes: a head body (distal end frame) formed of an MID element in which a plurality of electroconductive paths are formed; at least one electronic device to which an electric power is supplied through the electroconductive paths; and a camera module (image pickup unit).

SUMMARY OF THE INVENTION

A distal end frame of an endoscope according to one aspect of the present invention includes a first distal end frame member that includes a resin molded product which constitutes a molded interconnect device having a metal pattern formed on a surface of the resin molded product; a housing chamber that is provided on a distal end side of the first distal end frame member, and is formed of a recessed portion a distal end and one side of which are opened; a second distal end frame member that is joined to the first distal end frame member and closes the one side of the housing chamber; one or more first metal patterns that are formed of the metal pattern constituting the molded interconnect device and are formed in a region including a joining portion with the second distal end frame member, on a surface of the first distal end frame member; and a joining member configured to join the first distal end frame member and the second distal end frame member to each other.

In addition, a distal end unit of an endoscope according to one aspect of the present invention includes a distal end frame, and an image pickup unit provided in a housing chamber, wherein the distal end frame includes: a first distal end frame member that includes a resin molded product which constitutes a molded interconnect device having a metal pattern formed on a surface of the resin molded product; the housing chamber that is provided on a distal end side of the first distal end frame member, and is formed of a recessed portion a distal end and one side of which are opened; a second distal end frame member that is joined to the first distal end frame member and closes the one side of the housing chamber; one or more first metal patterns that are formed of the metal pattern constituting the molded interconnect device and are formed in a region including a joining portion with the second distal end frame member, on a surface of the first distal end frame member; and a joining member configured to join the first distal end frame member and the second distal end frame member to each other.

In addition, an endoscope according to one aspect of the present invention includes a distal end frame and an image pickup unit provided in a housing chamber, wherein the distal end frame includes: a first distal end frame member that includes a resin molded product which constitutes a molded interconnect device having a metal pattern formed on a surface of the resin molded product; the housing chamber that is provided on a distal end side of the first distal end frame member, and is formed of a recessed portion a distal end and one side of which are opened; a second distal end frame member that is joined to the first distal end frame member and closes the one side of the housing chamber; one or more first metal patterns that are formed of the metal pattern constituting the molded interconnect device and are formed in a region including a joining portion with the second distal end frame member, on a surface of the first distal end frame member; and a joining member configured to join the first distal end frame member and the second distal end frame member to each other.

DETAILED DESCRIPTION OF THE PREFERRED EMBODIMENTS

Figure 1:
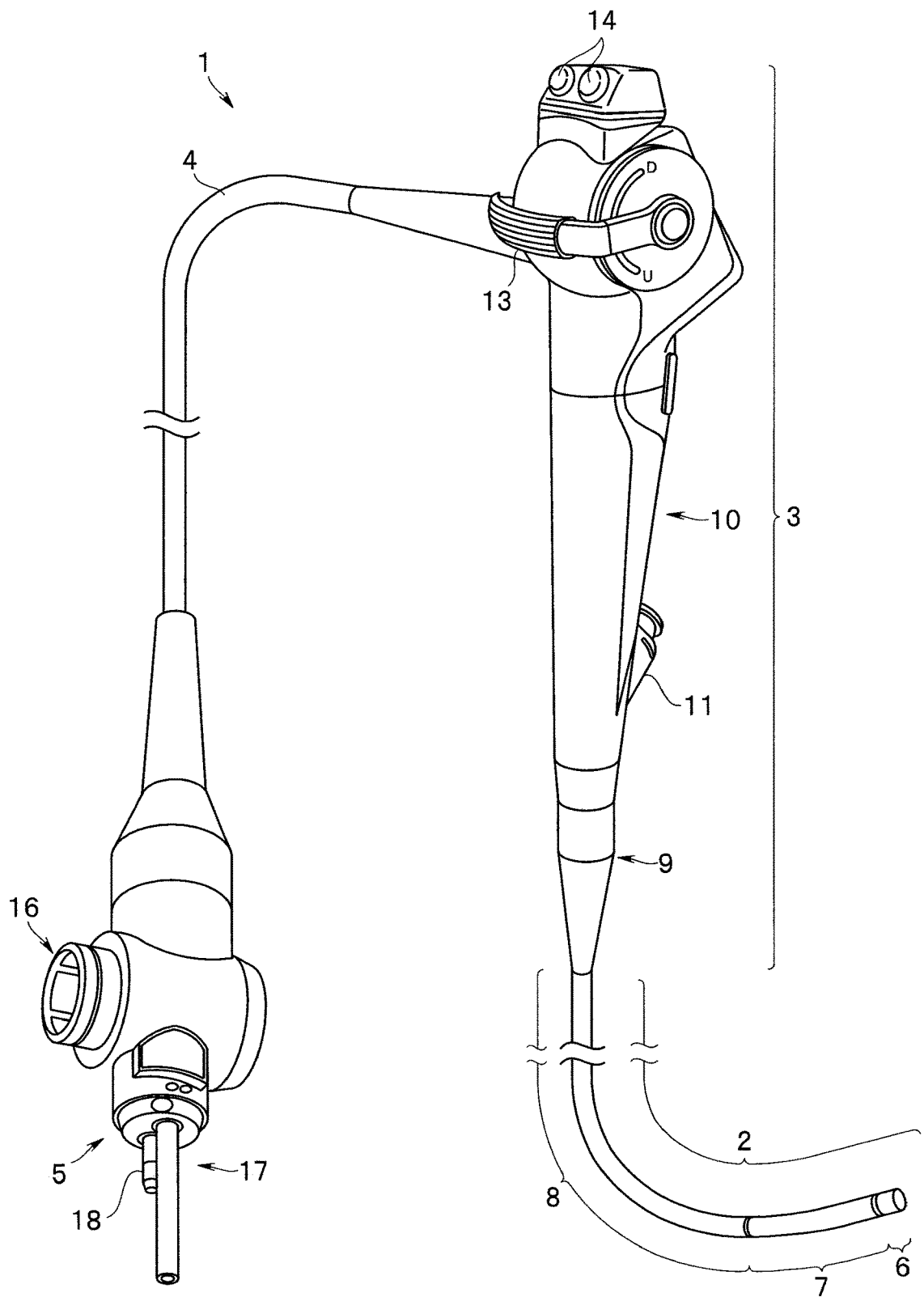
FIG. 1 is an external perspective view of an endoscope according to a first embodiment of the present invention.

Embodiments of the present invention will be described below with reference to drawings. FIG. 1 to FIG. 8 relate to a first embodiment of the present invention, and FIG. 1 is an external perspective view of an endoscope.

An endoscope 1 shown in FIG. 1 includes: an insertion portion 2 with an elongated shape (long shape), which is inserted into a body cavity of a subject; an operation section 3 that is provided continuously to a proximal end of the insertion portion 2, a universal cable 4 that extends from the proximal end of the operation section 3; and an endoscope connector 5 that is arranged at an extending end of the universal cable 4.

The insertion portion 2 is a tubular member having flexibility, in which a distal end portion 6, a bending portion 7, and a flexible tube portion 8 are continuously provided in this order from the distal end side.

Figure 2:
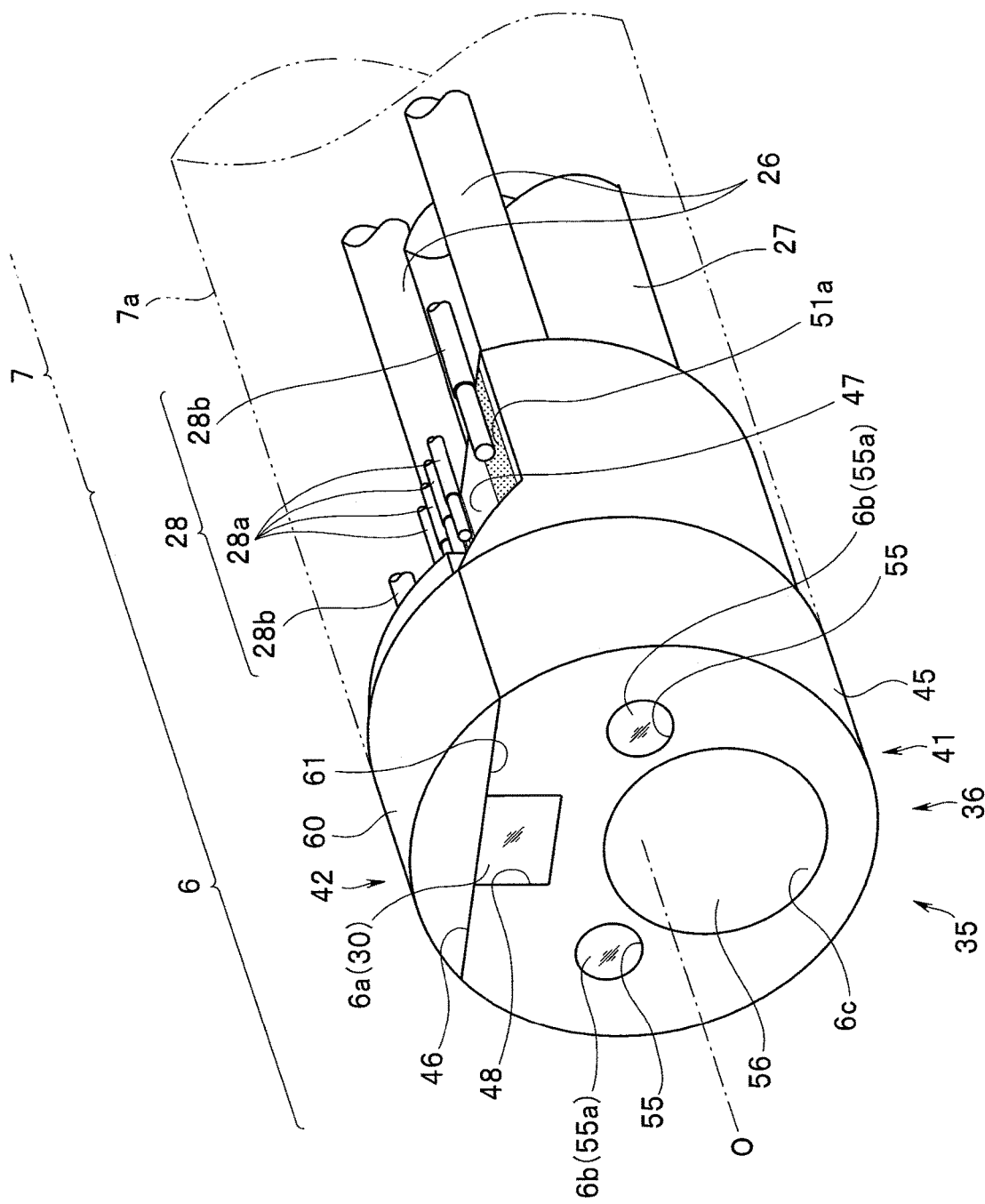
FIG. 2 is a perspective view showing a distal end unit according to the first embodiment of the present invention, from a distal end side.
Figure 3:
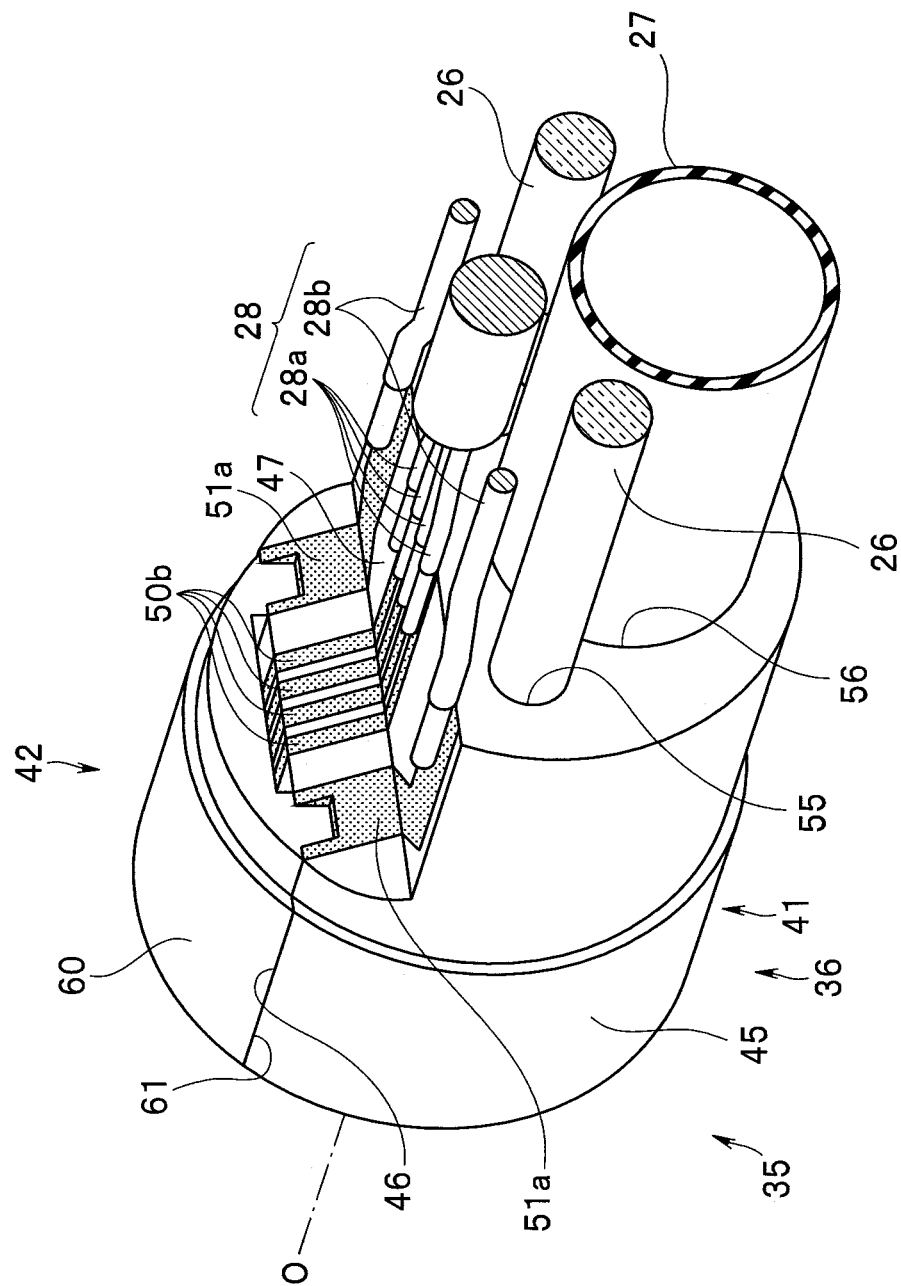
FIG. 3 is a perspective view showing the distal end unit according to the first embodiment of the present invention, from a proximal end side.

As shown in FIG. 2, for example, an observation window 6a through which a subject is observed, a pair of illumination windows 6b through which the subject is irradiated with illumination light, and a channel opening 6c with which the distal end side of a treatment instrument channel 27 communicates are arranged on the distal end surface of the distal end portion 6.

In addition, an image pickup unit 25 (see FIGS. 4 and 5) configured to pick up an optical image of the subject is arranged inside the distal end portion 6, and also the distal end side of a light guide 26 configured to guide illumination light to be applied to the subject, to the distal end portion 6 through the illumination window 6b, and the like are arranged.

The bending portion 7 is a mechanism site that is configured to be actively bent in, for example, two upward and downward bending directions (up-down). Note that in the present embodiment, up-and-down and left-and-right directions of the insertion portion 2 and the like are defined for convenience to correspond with up-and-down and left-and-right directions of an endoscope image to be picked up by the image pickup unit 25.

The flexible tube portion 8 is a tubular member that is configured to have flexibility to become passively flexible. Various cables 28 that are electrically connected to the image pickup unit 25 and the like, the light guide 26, the treatment instrument channel 27 and the like are inserted in an inside of the flexible tube portion 8.

The operation section 3 includes: a bend preventing portion 9 that is connected to the flexible tube portion 8 in a state of covering the proximal end of the flexible tube portion and a grip portion 10 that is provided continuously to the proximal end side of the bend preventing portion 9 and can be gripped by the hand of a user.

A treatment instrument insertion portion 11 that communicates with the proximal end side of the treatment instrument channel 27 is provided on the distal end side of the grip portion 10. In addition, an operation lever 13 for performing a bending operation of the bending portion 7, and operation switches 14 to which various functions of the endoscope 1 are assigned are provided on the proximal end side of the grip portion 10.

The universal cable 4 is a composite cable that allows insertion of, for example, the various cables 28, the light guide 26 and the like extending from the distal end portion 6 of the insertion portion 2, inside, and that also allows insertion of an air/water feeding tube (not illustrated) the distal end side of which is connected to the treatment instrument channel 27, inside.

The endoscope connector 5 includes: an electrical connector portion 16 configured to connect various cables 28 to a video processor (not illustrated) which is an external device; a light source connector portion 17 configured to connect the light guide 26 to a light source device (not illustrated) which is an external device; and an air/water feeding plug 18 configured to connect an air/water feeding tube to an air/water feeding device (not illustrated) which is an external device.

Next, a configuration of the distal end portion 6 will be specifically described with reference to FIG. 2 to FIG. 6.

The distal end portion 6 of the present embodiment is mainly composed of a distal end unit 35 that has various functional components such as the image pickup unit 25 provided in a distal end frame 36 having a hard and approximately columnar shape formed of molded interconnect devices (MIDs).

Figure 4:
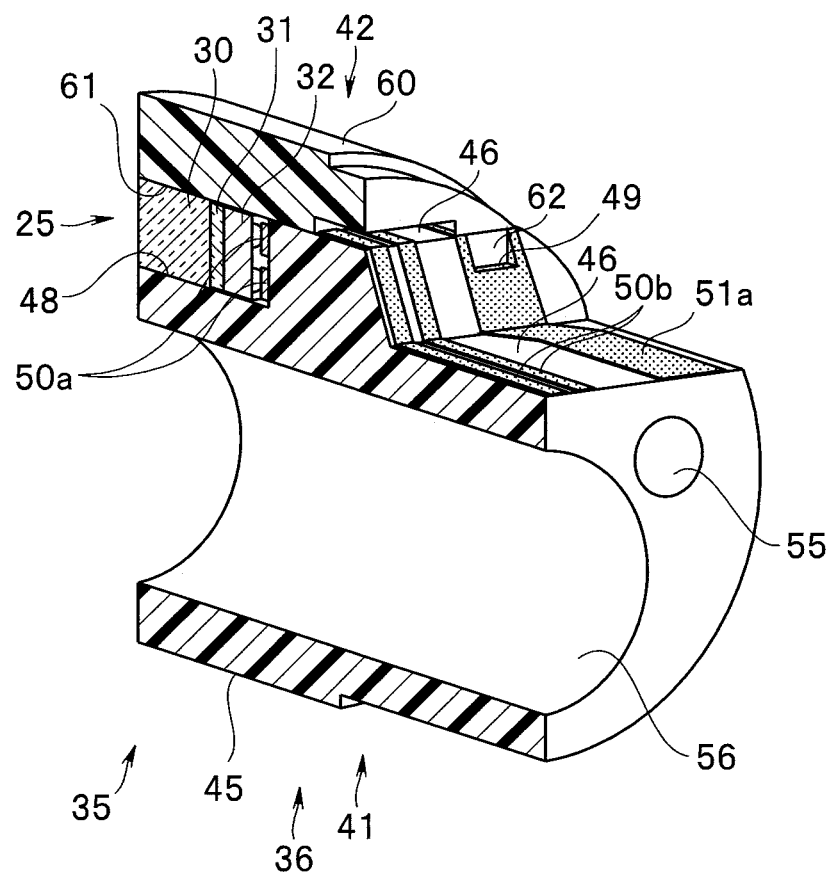
FIG. 4 is a cross-sectional view showing a main part of the distal end unit according to the first embodiment of the present invention, along a line IV-IV in FIG. 3.
Figure 5:
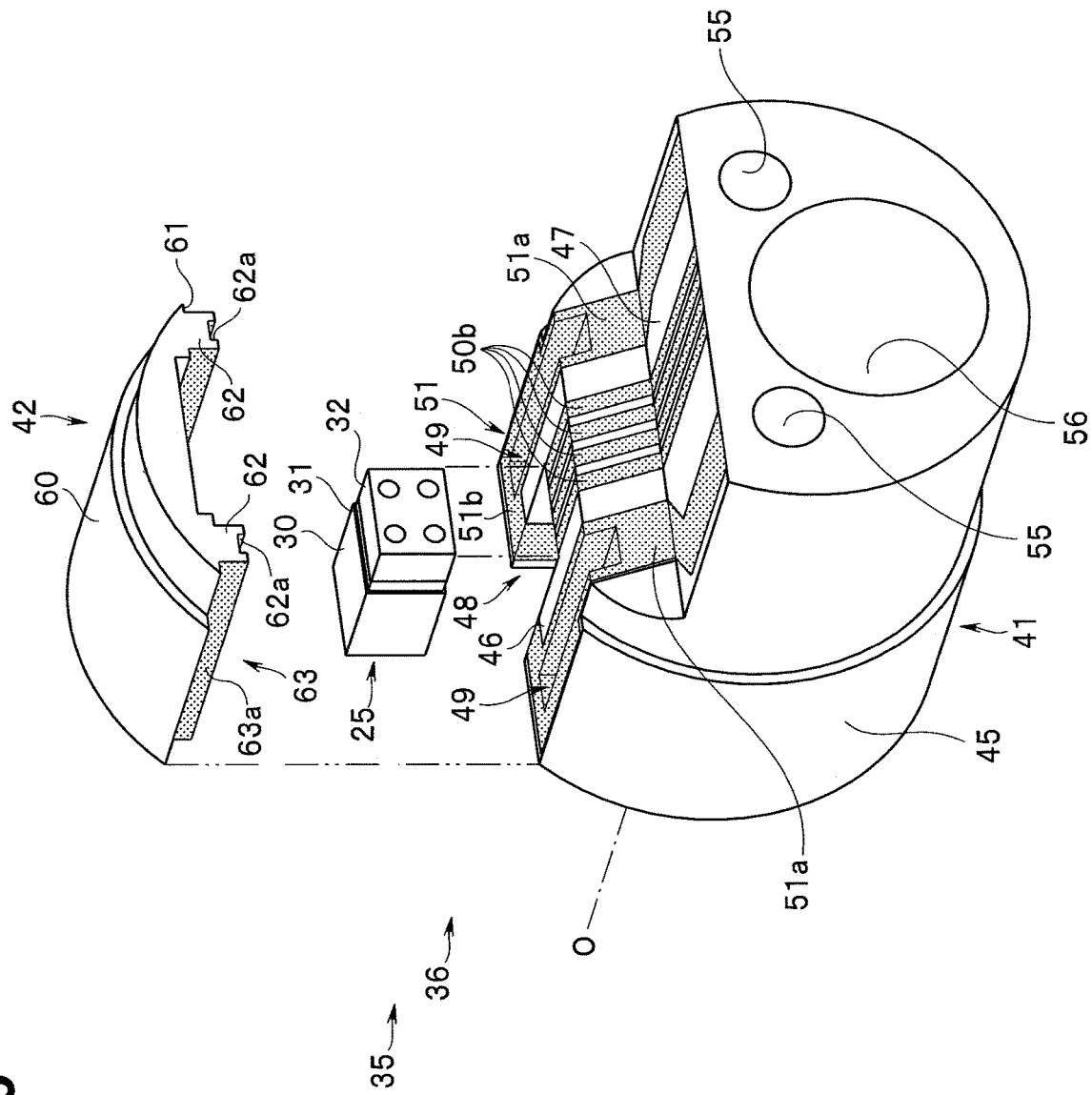
FIG. 5 is an exploded perspective view showing the main part of the distal end unit according to the first embodiment of the present invention.

Here, in the present embodiment, for example, as shown in FIGS. 4 and 5, the image pickup unit 25 provided in the distal end frame 36 as one of the functional components is composed of a CSP (chip size package) in which a lens unit 30 for image pickup composed of a lens laminate formed with the use of a wafer-level optics technique, a cover glass 31, and an image pickup device 32 that is connected to the lens unit 30 for image pickup stuck on the cover glass 31 via an adhesive layer (not illustrated) are integrally packaged. In such an image pickup unit 25, the lens unit 30 for image pickup is manufactured, for example, by preparing a plurality of lens wafers in which lenses are formed on a base material such as a glass substrate, and stacking and dicing the lens wafers. Because of this, the lens unit 30 for image pickup of the present embodiment is a lens unit that has a rectangular shape in plan view and does not have a lens frame. In addition, the image pickup device 32 is also formed into a rectangular shape in plan view by dicing or the like, and the image pickup unit 25 of the present embodiment has an approximately rectangular parallelepiped shape as a whole.

The distal end frame 36 includes a first distal end frame member 41 and a second distal end frame member 42 which are each formed of a resin molded product constituting the MID.

The first distal end frame member 41 and the second distal end frame member 42 in the present embodiment has a shape which has been obtained, for example, by dividing the distal end frame 36 having an approximately columnar shape into two upper and lower portions in the extending direction of an insertion axis O, on an upper side of a center portion (insertion axis O).

Figure 6:
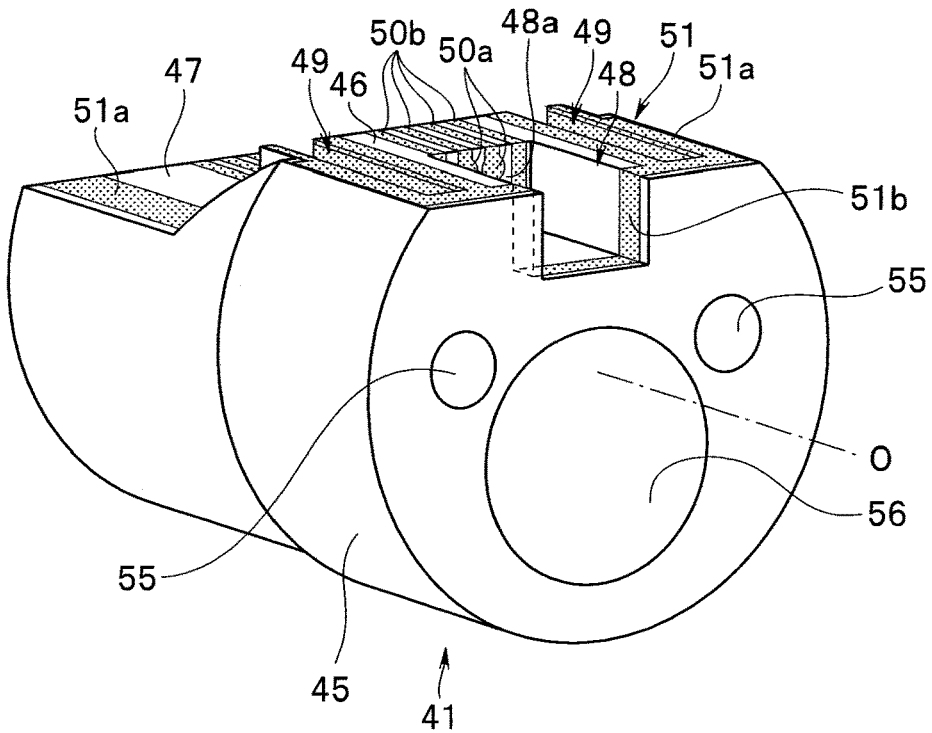
FIG. 6 is a perspective view showing a first distal end frame member according to the first embodiment of the present invention, from the distal end side.
Figure 7:
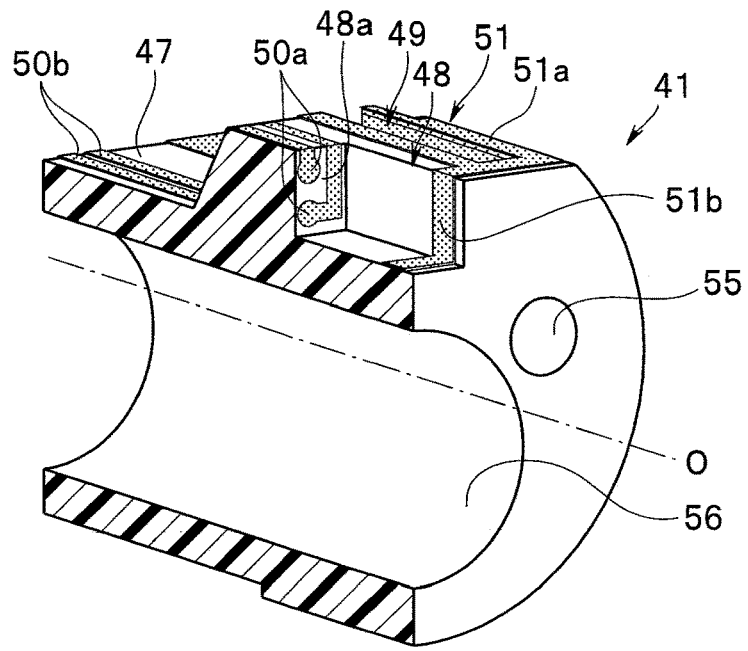
FIG. 7 is a cross-sectional view showing the first distal end frame member according to the first embodiment of the present invention, along a line VII-VII in FIG. 6.

In other words, for example, as shown in FIG. 5 to FIG. 7, the first distal end frame member 41 forms an appearance of an approximately partially columnar shape, which has a first outer periphery forming surface 45 that forms a part of an outer peripheral surface of the distal end frame 36 and has a partially arc shape in the cross section, and a first joining surface 46 that is a joining surface with the second distal end frame member 42, formed on the outer periphery. Furthermore, a notch-shaped step is provided on the proximal end side of the first joining surface 46, and a flat surface formed by the step is set as a cable connection surface 47 configured to connect various cables 28.

An image pickup unit housing chamber 48 configured to house the image pickup unit 25 is formed in the first distal end frame member 41.

The image pickup unit housing chamber 48 is composed of a recessed portion having an approximately rectangular shape the distal end of which opens to the distal end surface of the first distal end frame member 41 and one side opens to the first joining surface 46.

In the image pickup unit housing chamber 48, a surface on the proximal end side in the insertion axis O direction is set as a mounting surface 48a on which the image pickup unit 25 is mounted.

On the mounting surface 48a, a plurality of (for example, four) connection lands 50a are provided as a first metal pattern. The image pickup device 32 is electrically connected to each of the connection lands 50a by a material having electroconductivity. Note that as the material having the electroconductivity for electrically connecting the image pickup device 32 to each of the connection lands 50a, solder, an electroconductive adhesive or the like can be suitably used.

Furthermore, signal patterns 50b as the first metal pattern are connected to the respective connection lands 50a. Each of the signal patterns 50b is extended from the mounting surface 48a to the proximal end side of the cable connection surface 47 via the first joining surface 46, and is electrically connected to the signal cable 28a (cable 28) that is inserted through the insertion portion 2, by solder connection.

On both sides of the image pickup unit housing chamber 48, the first joining surface 46 is provided with fitting recesses 49 configured to position the first distal end frame member 41 and the second distal end frame member 42.

Furthermore, a first shield pattern 51 as the first metal pattern is provided in a predetermined region including the first joining surface 46, on the surface of the first distal end frame member 41.

The first shield pattern 51 includes: a pair of first wiring portions 51a that extend in the insertion axis O direction on both sides of the image pickup unit housing chamber 48; and a second wiring portions 51b that extends in a direction intersecting (for example, orthogonal to) the insertion axis O in a region including an inner surface of the image pickup unit housing chamber 48.

Each of the first wiring portions 51a is formed in a band shape to cover the surface of the fitting recess 49, and is connected to each other by the second wiring portion 51b on the distal end side with respect to the image pickup device 32. In addition, each of the first wiring portions 51a is extended from the first joining surface 46 to the proximal end side of the cable connection surface 47, and is electrically connected to a shielded cable 28b (cable 28) that is inserted through the insertion portion 2, by the solder connection.

Here, each of the connection lands 50a, each of the signal patterns 50b, and the first shield pattern 51 are formed by an MID technology, and for example, are formed, after a resin surface which forms the first distal end frame member 41 is activated by laser irradiation or the like, by metal plating being performed onto the resin surface which has been activated.

In addition, as for a solder material that is used for solder joining of the image pickup device 32, the signal cable 28a, the shielded cable 28b and the like, a lead-free solder material is desirable, and for example, an Sn—Ag—Cu-based solder material having a melting point of about 230 degrees is suitably used.

Furthermore, in an inside of the first distal end frame member 41, there are formed a light source housing chamber 55 as a housing chamber configured to house the distal end side of the light guide 26 that is an optical functional component, and a channel holding chamber 56 configured to hold the distal end side of the treatment instrument channel 27.

The light source housing chamber 55 is composed, for example, of a through hole extending in the insertion axis O direction of the insertion portion 2. The light source housing chamber 55 is a circular hole a cross-sectional shape in a direction orthogonal to the insertion axis O of which is an approximately circular shape.

The light guide 26 is inserted into the light source housing chamber 55. Furthermore, an optical member 55a formed of an illumination lens, a cover glass or the like is attached to the light source housing chamber 55 on the distal end side with respect to the light guide 26, the optical member 55a closes the distal end side of the light source housing chamber 55, and thereby an illumination window 6b is formed on the distal end surface of the first distal end frame member 41.

The channel holding chamber 56 is composed of a through hole extending in the insertion axis O direction of the insertion portion 2. The channel holding chamber 56 is a circular hole a cross-sectional shape in the direction vertical to the insertion axis O of which is an approximately circular shape.

In the channel holding chamber 56, the treatment instrument channel 27 is fixed via an unillustrated pipe sleeve. In addition, the channel opening 6c is formed at the distal end side of the channel holding chamber 56.

Figure 8:
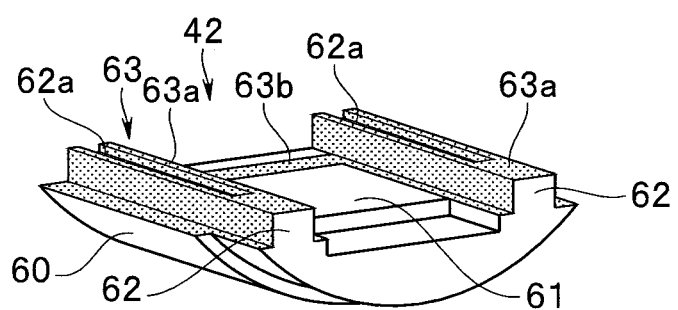
FIG. 8 is a perspective view showing a second distal end frame member according to the first embodiment of the present invention, from a joining surface side.

For example, as shown in FIG. 5 and FIG. 8, the second distal end frame member 42 has an appearance of an approximately partially columnar shape, which has a second outer periphery forming surface 60 that forms another part of an outer peripheral surface of the distal end frame 36 and has an approximately partially arc shape in the cross section, and a second joining surface 61 that is a joining surface with the first distal end frame member 41 (first joining surface 46), formed on the outer periphery.

On the second joining surface 61 of the second distal end frame member 42, fitting salients 62 configured to position the second distal end frame member 42 and the first distal end frame member 41 are provided at positions corresponding to the fitting recesses 49. In addition, a groove portion 62a is provided on a protruding end face of each of the fitting salients 62.

Furthermore, a second shield pattern 63 as a second metal pattern is provided in a predetermined region on the second joining surface 61.

The second shield pattern 63 includes: a pair of third wiring portions 63a that extend in the direction of the insertion axis O to correspond to the pair of first wiring portions 51a, respectively; and a fourth wiring portion 63b that extends in the direction intersecting the insertion axis O to correspond to the second wiring portion 51b.

Each of the third wiring portions 63a are formed in a band shape to cover the surface of each of the fitting salients 62, and are connected to each other by the fourth wiring portion 63b, on the distal end side with respect to the image pickup device 32 held in the image pickup unit housing chamber 48.

Here, the second shield pattern 63 is formed by the MID technology, and for example, is formed, after the resin surface which forms the second distal end frame member 42 is activated by laser irradiation or the like, by metal plating being performed onto the resin surface which has been activated.

The first wiring portion 51a formed on the first joining surface 46 and the third wiring portion 63a formed on the second joining surface 61 are joined by solder, and thereby, the first distal end frame member 41 and the second distal end frame member 42 are joined to each other, and constitute the distal end frame 36 that forms an approximately columnar shape as a whole.

In other words, the first wiring portion 51a that constitutes the first shield pattern 51 and the third wiring portion 63a that constitutes the second shield pattern 63 function as metal patterns at the time when the first distal end frame member 41 and the second distal end frame member 42 are joined to each other by solder.

Furthermore, the first wiring portion 51a and the third wiring portion 63a are electrically connected to each other by solder joining, and thereby the second wiring portion 51b of the first shield pattern 51 and the fourth wiring portion 63b of the second shield pattern 63 form an electromagnetic shield surrounding the outer periphery of the image pickup unit 25 on the distal end side with respect to the image pickup device 32.

At the time, the fitting salients 62 are fitted into the fitting recesses 49, respectively, a sufficient joined area is secured, and at the same time, the first distal end frame member 41 and the second distal end frame member 42 are appropriately positioned. Note that the arrangement of the fitting recess and the fitting salient is not limited to the above example, and the fitting salient may be provided in the first distal end frame member 41 and the fitting recess may be provided in the second distal end frame member 42.

In addition, each of the fitting salients 62 has the groove portion 62a, and accordingly the excess solder between the first wiring portion 51a and the third wiring portion 63a is absorbed by the groove portion 62a.

Here, a solder material to be used for the solder joining between the first distal end frame member 41 and the second distal end frame member 42 is desirably a lead-free solder material, and for example, an Sn—Bi-based low-melting-point solder material is suitably used which has a melting point of about 140 degrees. In other words, in the present embodiment, the solder material for joining the first distal end frame member 41 and the second distal end frame member 42 has a lower melting point than the solder material to be used for solder joining of the image pickup device 32, the signal cable 28a, the shielded cable 28b and the like.

The first distal end frame member 41 and the second distal end frame member 42 are joined as in the above, and thereby, the signal patterns 50b and the first shield pattern 51 which are formed on the first joining surface 46 and the second shield pattern 63 which is formed on the second joining surface 61 are consequently formed in an inside of the distal end frame 36.

In other words, the distal end frame 36 of the present embodiment has a structure in which various wirings are not exposed to the outer peripheral surface in a region on the distal end side of the distal end frame 36. Accordingly, the region on the distal end side of the distal end frame 36 can be used as it is, as the outer surface of the distal end portion 6.

For the reason, a material that not only is compatible with the MID technology but also has biocompatibility is selected for a resinous material that forms the first distal end frame member 41 and the second distal end frame member 42.

Note that after the first distal end frame member 41 and the second distal end frame member 42 has been joined, the image pickup unit housing chamber 48 is filled with an unillustrated resinous adhesive agent or the like, and the image pickup unit 25 is fixed in an inside of the image pickup unit housing chamber 48 in a liquid-tight state. At the time, in the present embodiment, the distal end surface of the lens unit 30 for image pickup of the image pickup unit 25 is directly exposed to the distal end surface of the distal end frame 36 and functions as the observation window 6a.

In addition, the proximal end side of the distal end frame 36 is covered with an outer skin 7a or the like, which constitutes the bending portion 7, and thereby, the signal patterns Sob extending to the cable connection surface 47, the first wiring portion 51a, and the various cables 28 that are connected to the signal patterns 50b and the first wiring portion 51a are liquid-tightly protected.

According to such an embodiment, the distal end frame 36 includes the first distal end frame member 41 that is composed of the resin molded product constituting the molded interconnect device which has the metal pattern formed on the surface of the resin molded product, and on which the mourning surface 48a is formed on which the image pickup unit 25a is mounted, the second distal end frame member 42 that is composed of the resin molded product constituting the molded interconnect device and is configured to join with the first distal end frame member 41, the signal patterns 50b that are composed of a metal plated pattern constituting the molded interconnect device, and is the metal pattern formed in a region including the first joining surface 46 which is the joining surface with the second distal end frame member 42, on the surface of the first distal end frame member 41, and a solder material as a joining member configured to join the first distal end frame member 41 and the second distal end frame member and thereby can reduce a diameter of the distal end portion 6, while ensuring sufficient insulation properties.

In other words, by forming the main body portion of the distal end frame 36 by dividing the main body portion into the first distal end frame member 41 and the second distal end frame member 42, forming the signal patterns 50b to be electrically connected to the image pickup unit 25 in a region including the first joining surface 46, and sandwiching the resultant signal patterns 50b between the first joining surface 46 and the second joining surface 61, the signal patterns 50b can be formed without being exposed to an outer surface of the distal end frame 36. In addition, the first distal end frame member 41 and the second distal end frame member 42 are each the resin molded products constituting molded interconnect devices, and accordingly it is not necessary to cover the surface of the distal end frame 36 with an insulative cap or the like. Accordingly, it is possible to reduce the diameter of the distal end portion 6, while ensuring sufficient insulation properties.

In the case, by further forming the first shield pattern 51 in a region including the first joining surface 46, and also forming the second shield pattern 63 in a region including the second joining surface 61, the distal end frame 36 can electromagnetically shield the image pickup unit 25 and improve noise resistance, even when the first and second distal end frame members 41 and 42 that constitute the main body portion of the distal end frame 36 are each formed of the resin molded product.

In addition, by forming the first and second shield patterns 51 and 63 on the first and second joining surfaces 46 and 61, respectively, the first and second shield patterns 51 and 63 can also serve as metal layers when the first and second distal end frame members 41 and 42 are joined by solder.

In addition, as for a solder material for joining the first and second distal end frame members 41 and 42 by solder, the solder material is adopted that has a lower melting point than a solder material for joining the image pickup device 32, the signal cable 28a, the shielded cable 28b and the like to the distal end frame 36, and thereby the distal end frame 36 can be easily disassembled, and the image pickup unit 25 or the like can be easily taken out when being reused.

Figure 9:
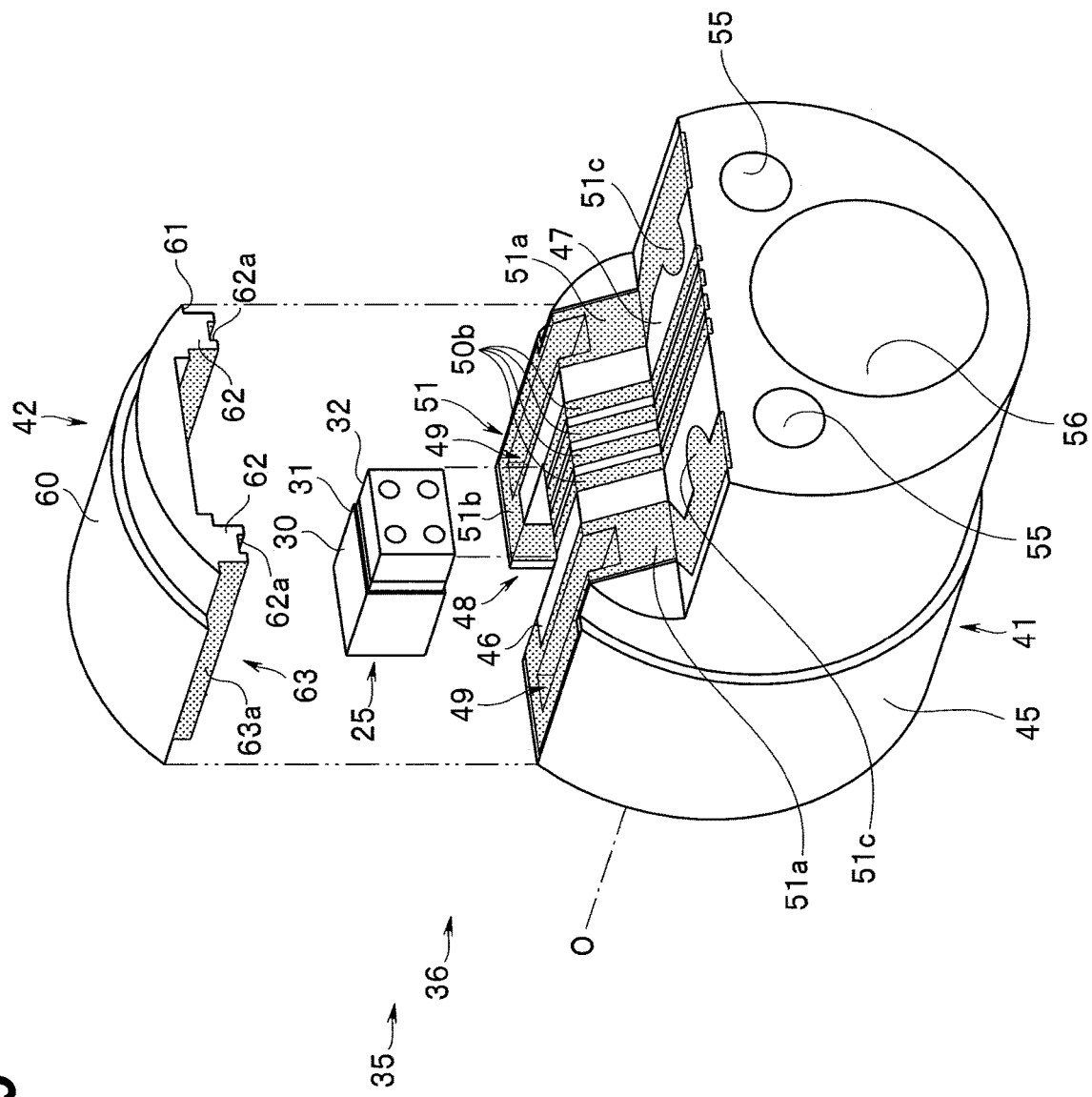
FIG. 9 is an exploded perspective view showing a main part of a distal end unit according to a first modification in the first embodiment of the present invention.
Figure 10:
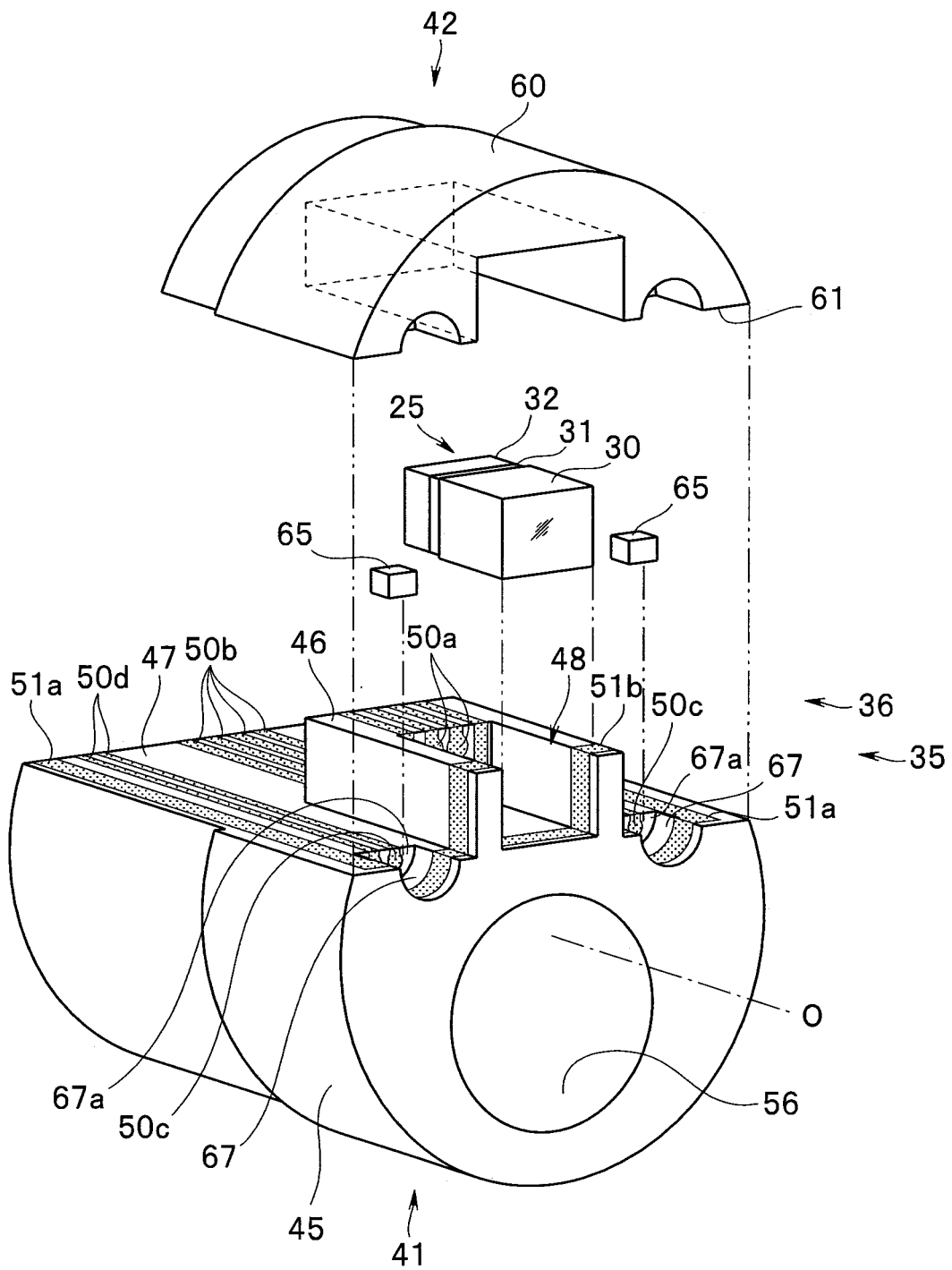
FIG. 10 is an exploded perspective view showing a main part of a distal end unit according to a second modification in the first embodiment of the present invention.

Here, for example, as shown in FIG. 9, it is also possible to form a pad 51c for thermal conduction in the first shield pattern 51, on the cable connection surface 47. When the pad 51c for the thermal conduction is heated, which has been configured as in the above, the pad 51c can efficiently transfer the heat to the solder material having the low melting point, which exists between the first wiring portion 51a of the first shield pattern 51 and the third wiring portion 63a of the second shield pattern 63, and the distal end frame 36 can be more easily disassembled, when the image pickup unit 25 or the like is reused.

In addition, for example, in a case where a light emitting element 65 is used as the light source in place of the light guide 26, it is possible to cause a boundary portion at the time when the distal end frame 36 is divided into the first distal end frame member 41 and the second distal end frame member 42 to include a light source housing chamber 67.

In the case, by forming the light source housing chamber 67 by a bottomed hole portion, setting the proximal end surface of the divided light source housing chamber 67 to a mounting surface 67a of the light emitting element 65, forming a connection pad 50c, and also forming a signal pattern 50d in a region including the first joining surface 46, the signal pattern 50d can be formed without being exposed to the outer surface of the distal end frame 36, even when the light emitting element 65 is provided in the distal end unit 35.

Figure 11:
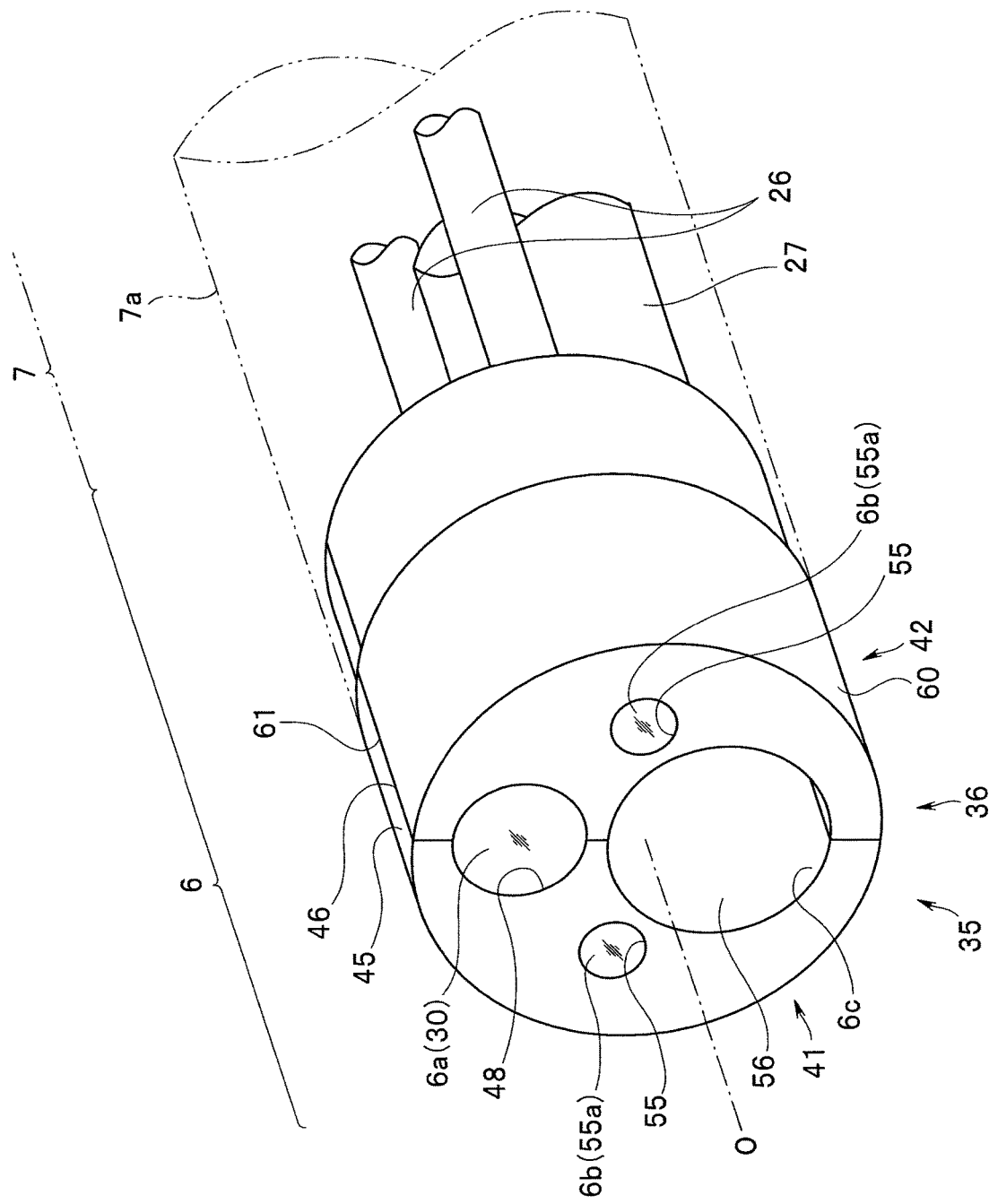
FIG. 11 is a perspective view showing a distal end unit according to a second embodiment of the present invention, from a distal end side.
Figure 12:
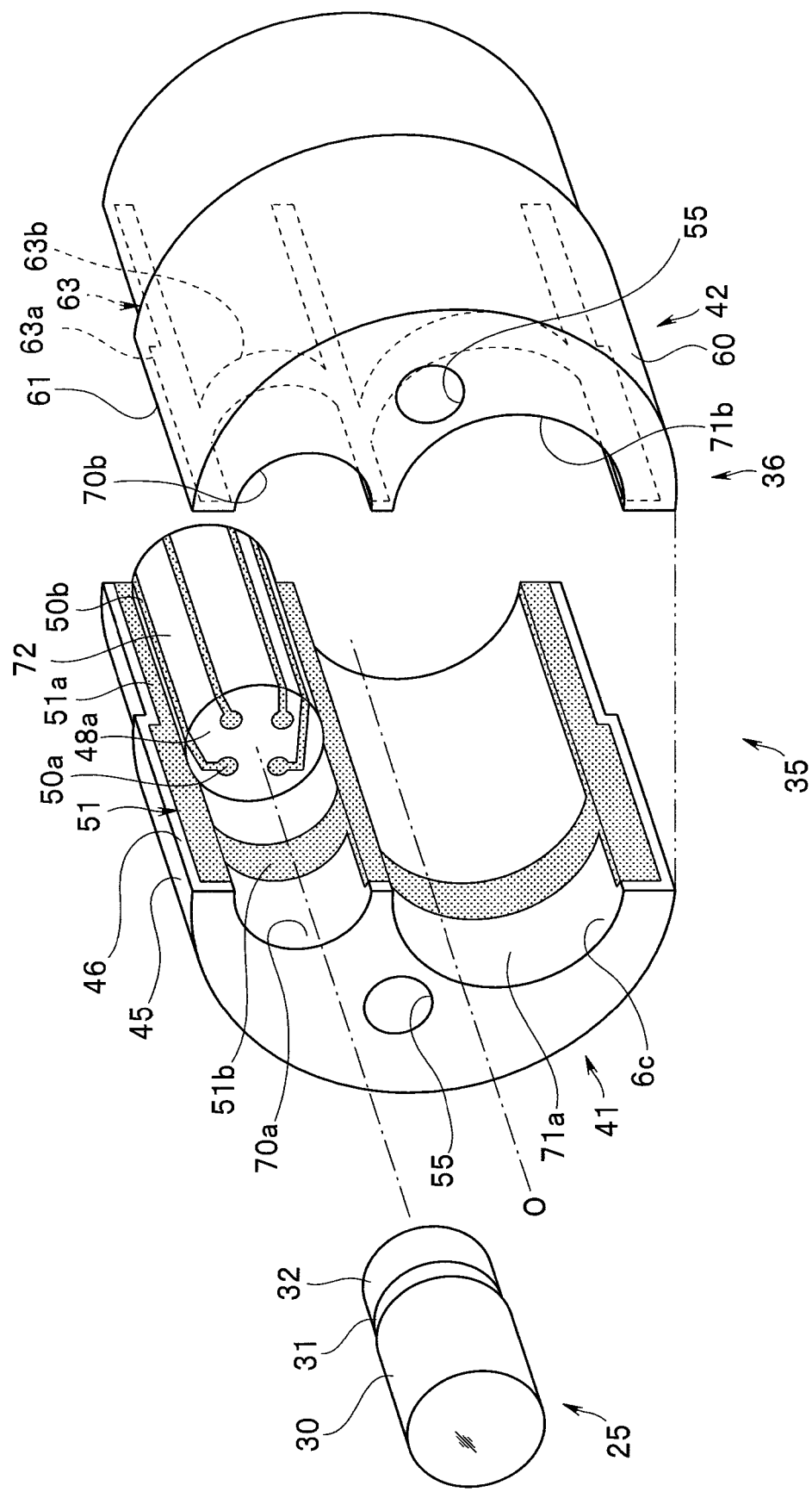
FIG. 12 is an exploded perspective view showing a main part of the distal end unit according to the second embodiment of the present invention.

Next, FIGS. 11 and 12 relate to a second embodiment of the present invention; FIG. 11 is a perspective view showing a distal end unit from the distal end side; and FIG. 12 is an exploded perspective view showing a main part of the distal end unit.

Here, in the above first embodiment, the configuration has been described in which the distal end frame 36 having the approximately columnar shape is divided into two upper and lower portions in the extending direction of the insertion axis O at a position offset from the center portion (insertion axis O), but the present embodiment is mainly different in that the distal end frame 36 having the approximately cylindrical shape is divided into two left and right portions in the extending direction of the insertion axis O at the center portion (position coinciding with insertion axis O). As for other components similar to the first embodiment described above, same signs will be appropriately added and the description will be omitted.

Note that in the present embodiment, the image pickup unit 25 is formed into an approximately columnar shape, and the observation window 6a and the like also have shapes corresponding to the image pickup unit 25.

In the present embodiment, the distal end frame 36 includes a first distal end frame member 41 and a second distal end frame member 42 which are divided into the left and right along a flat surface that passes through the insertion axis O, the center of the observation window 6a and the center of the channel opening 6c, and extends in the insertion axis O direction. In other words, the first distal end frame member 41 and the second distal end frame member 42 of the present embodiment each have an approximately semi-columnar shape.

In the first distal end frame member 41, there are formed a first recessed groove 70a for the image pickup unit, which is configured to form an image pickup unit housing chamber 48, and a first recessed groove 71a for a channel, which is configured to form a channel holding chamber 56. The first joining surface 46 is divided into three regions by the first recessed groove 70a for the image pickup unit and the first recessed groove 71a for the channel being formed.

The first recessed groove 70a for the image pickup unit has an approximately semi-circular shape in a cross-sectional shape, the distal end side is opened up, and the proximal end side is closed. Furthermore, a protruding portion 72 having a semi-columnar shape is provided continuously to a proximal end of the first recessed groove 70a for the image pickup unit. At the proximal end of the first recessed groove 70a for the image pickup unit, a region including the distal end surface of the protruding portion 72 is set as a mounting surface 48a on which the image pickup unit 25 is mounted.

In the mounting surface 48a, a plurality of (for example, four) connection lands 50a are provided as a first metal pattern. The image pickup device 32 is electrically connected to each of the connection lands 50a by solder connection.

Furthermore, signal patterns 50b as the first metal pattern are connected to the respective connection lands 50a. Each of the signal patterns 50b is extended from the mounting surface 48a to the proximal end side via a side surface of the protruding portion 72.

In addition, a first shield pattern 51 as the first metal pattern is provided in a predetermined region including the first joining surface 46, on a surface of the first distal end frame member 41.

The first shield pattern 51 includes: first wiring portions 51a each extending in the insertion axis O direction in three regions on the first joining surface 46, and a second wiring portions 51b extending in a direction intersecting for example, orthogonal to) the insertion axis O.

Here, the second wiring portion 51b is provided on the first recessed groove 70a for the image pickup unit and on the recessed groove 71a for the channel, and electrically connects the three regions of the first wiring portion 51a to each other.

In the second distal end frame member 42, there are formed a second recessed groove 70b for the image pickup unit, which is configured to form the image pickup unit housing chamber 48, and a second recessed groove 71b for the channel, which is configured to form the channel holding chamber 56. A second joining surface 61 is divided into three regions by the second recessed groove 70b for the image pickup unit and the second recessed groove 71b for the channel being formed.

The distal end side and the proximal end side of the second recessed groove 70b for the image pickup unit are opened up, and the protruding portion 72 can be fitted into the proximal end side.

In addition, a second shield pattern 63 as a second metal pattern is provided in a predetermined region including the second joining surface 61, on a surface of the second distal end frame member 42.

The second shield pattern 63 includes third wiring portions 63a each extending in the insertion axis O direction in three regions on the second joining surface 61, and a fourth wiring portion 63b extending in a direction intersecting (for example, orthogonal to) the insertion axis O.

Here, the fourth wiring portion 63b is provided on the second recessed groove 70b for the image pickup unit and on the second recessed groove 71b for the channel, and electrically connects the three regions of the third wiring portion 63a to each other.

The first wiring portion 51a formed on the first joining surface 46 and the third wiring portion 63a formed on the second joining surface 61 are joined by solder, and thereby, the first distal end frame member 41 and the second distal end frame member 42 are joined to each other, and constitute the distal end frame 36 that forms the approximately columnar shape as a whole. Note that also in the solder joining between such a first distal end frame member 41 and a second distal end frame member 42, it is desirable to use the solder material having the melting point lower than the inciting point of the solder material that is used in the solder joining for other portions.

Also in such an embodiment, substantially the same action effect as the action effect in the first embodiment described above can be achieved.

A shape of the image pickup unit 25 (and the observation window 6a and the like) can be variously modified according to the use of the endoscope 1, the layout of the distal end portion 6, and the like.

Figure 13:
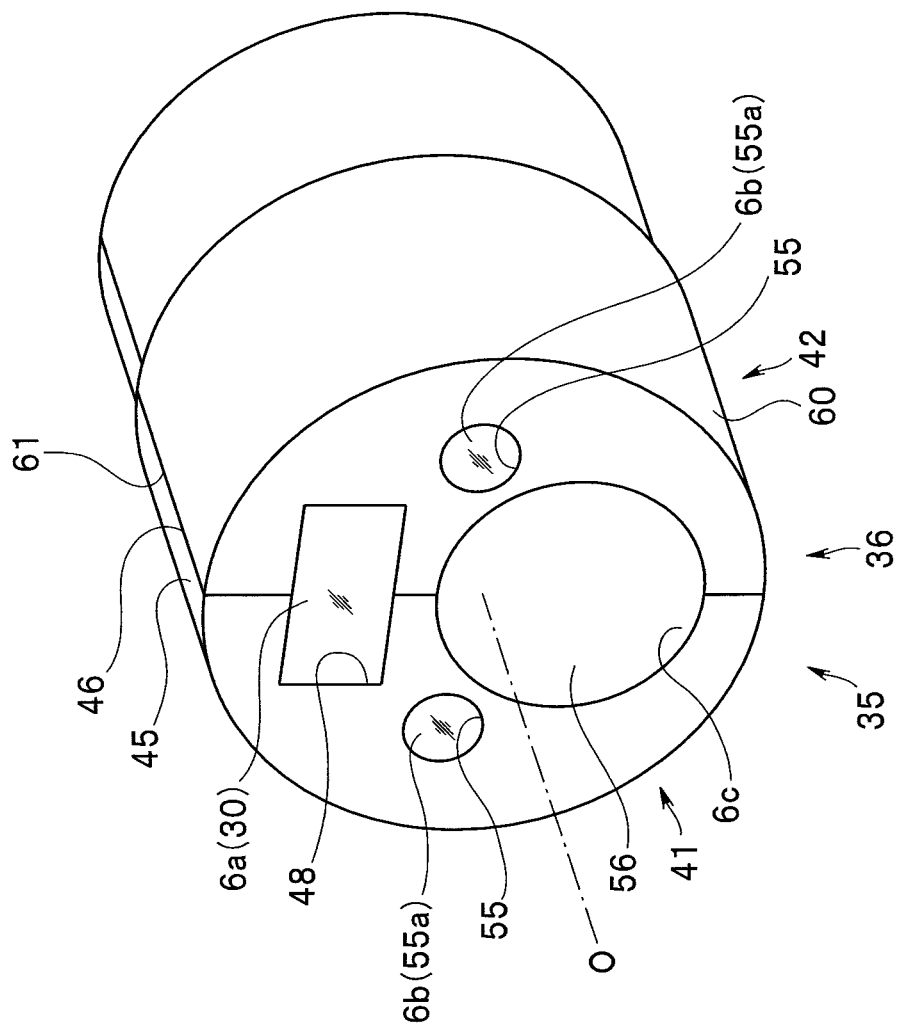
FIG. 13 is a perspective view showing a distal end unit according to a first modification in the second embodiment of the present invention, from a distal end side.

For example, as shown in FIG. 13, the shape in plan view of the image pickup unit 25 (and the observation window 6a and the like) can be a rectangular shape that is wide in the left-right direction.

Figure 14:
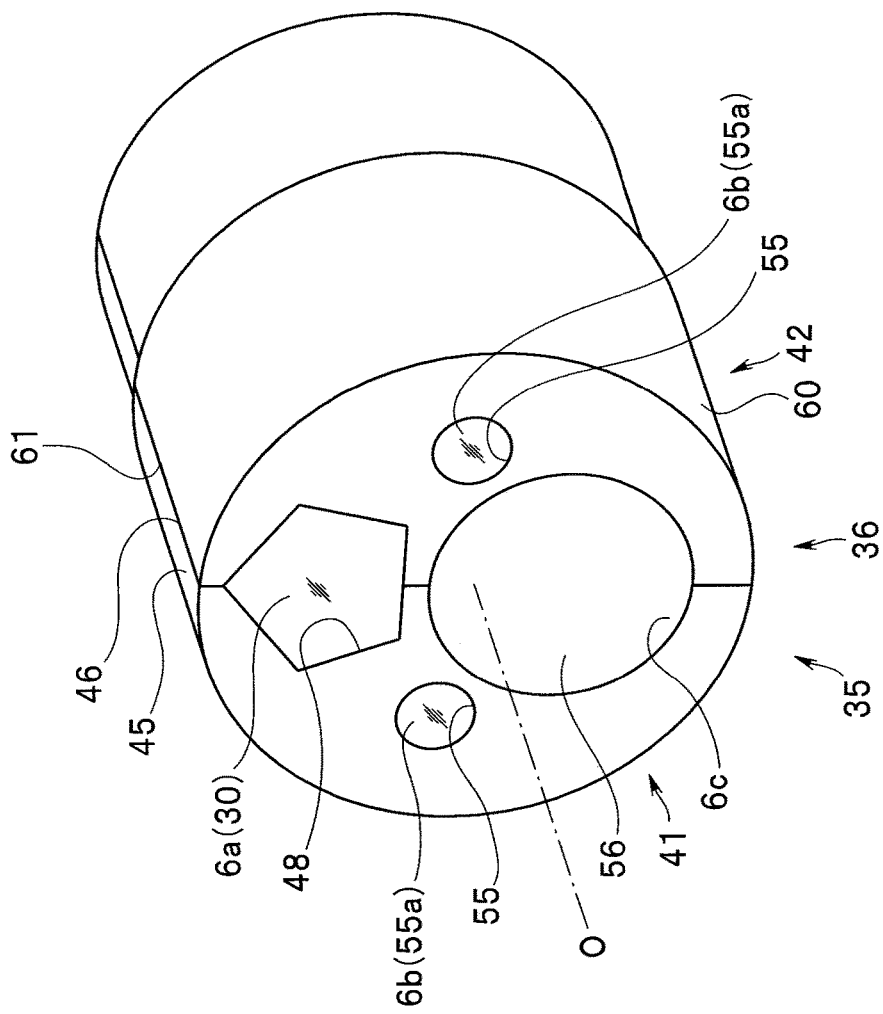
FIG. 14 is a perspective view showing a distal end unit according to a second modification in the second embodiment of the present invention, from a distal end side.

Alternatively, for example, as shown in FIG. 14, the shape in plan view of the image pickup unit 25 (and the observation window 6a and the like) can be a polygon (for example, a pentagon) other than the rectangle.

Figure 15:
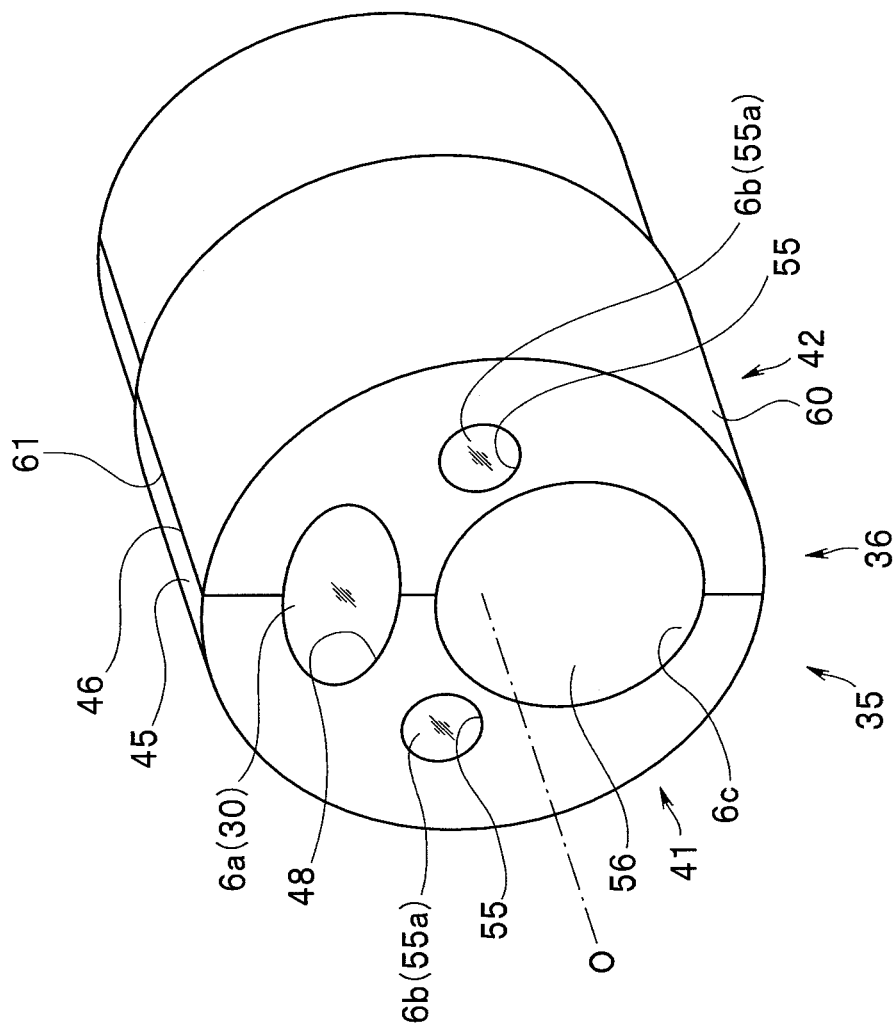
FIG. 15 is a perspective view showing a distal end unit according to a third modification in the second embodiment of the present invention, from a distal end side.

Alternatively, for example, as shown in FIG. 15, the shape in plan view of the image pickup unit 25 (and the observation window 6a and the like) can be an elliptical shape.

Figure 16:
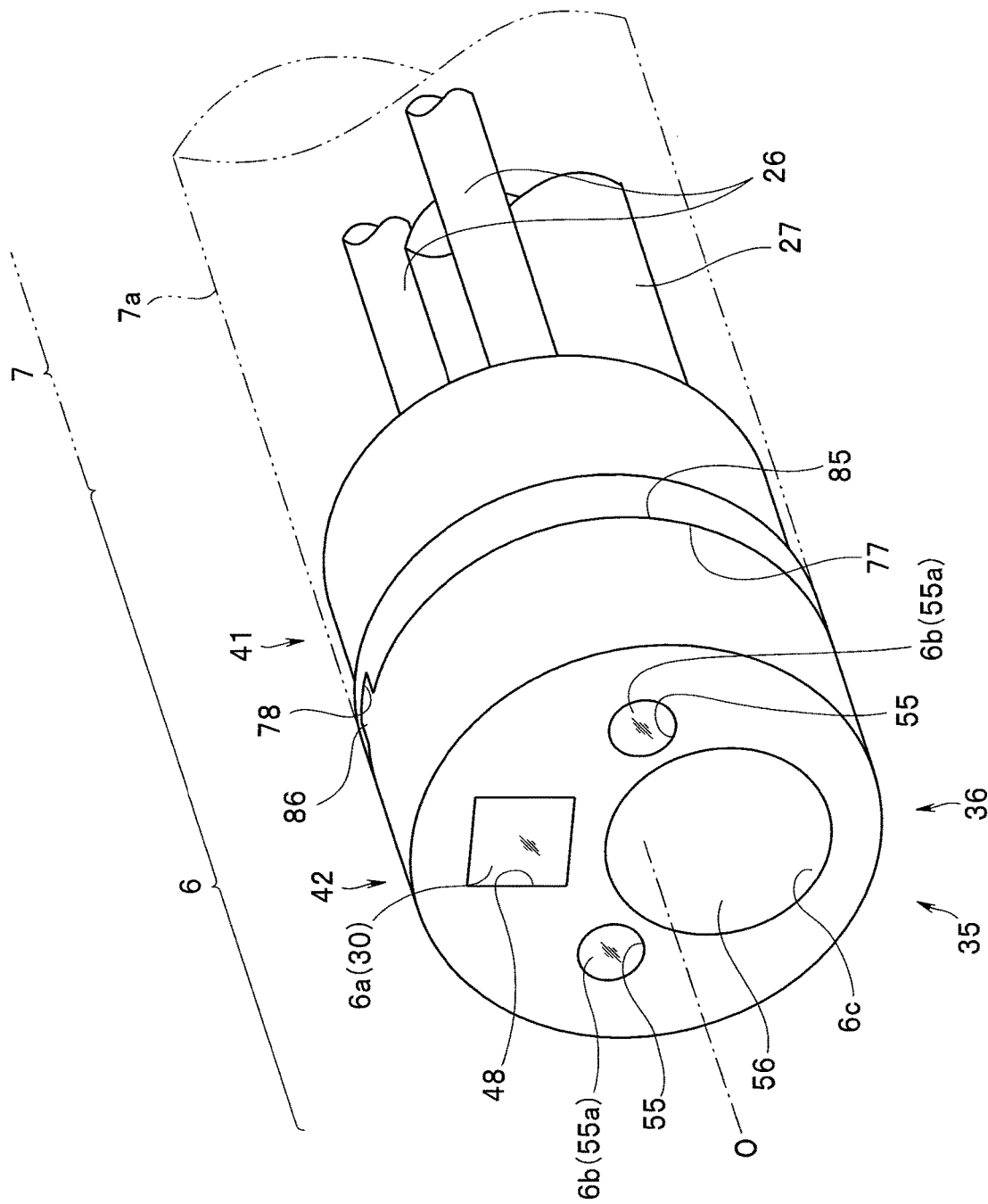
FIG. 16 is a perspective view showing a distal end unit according to a third embodiment of the present invention, from a distal end side.
Figure 17:
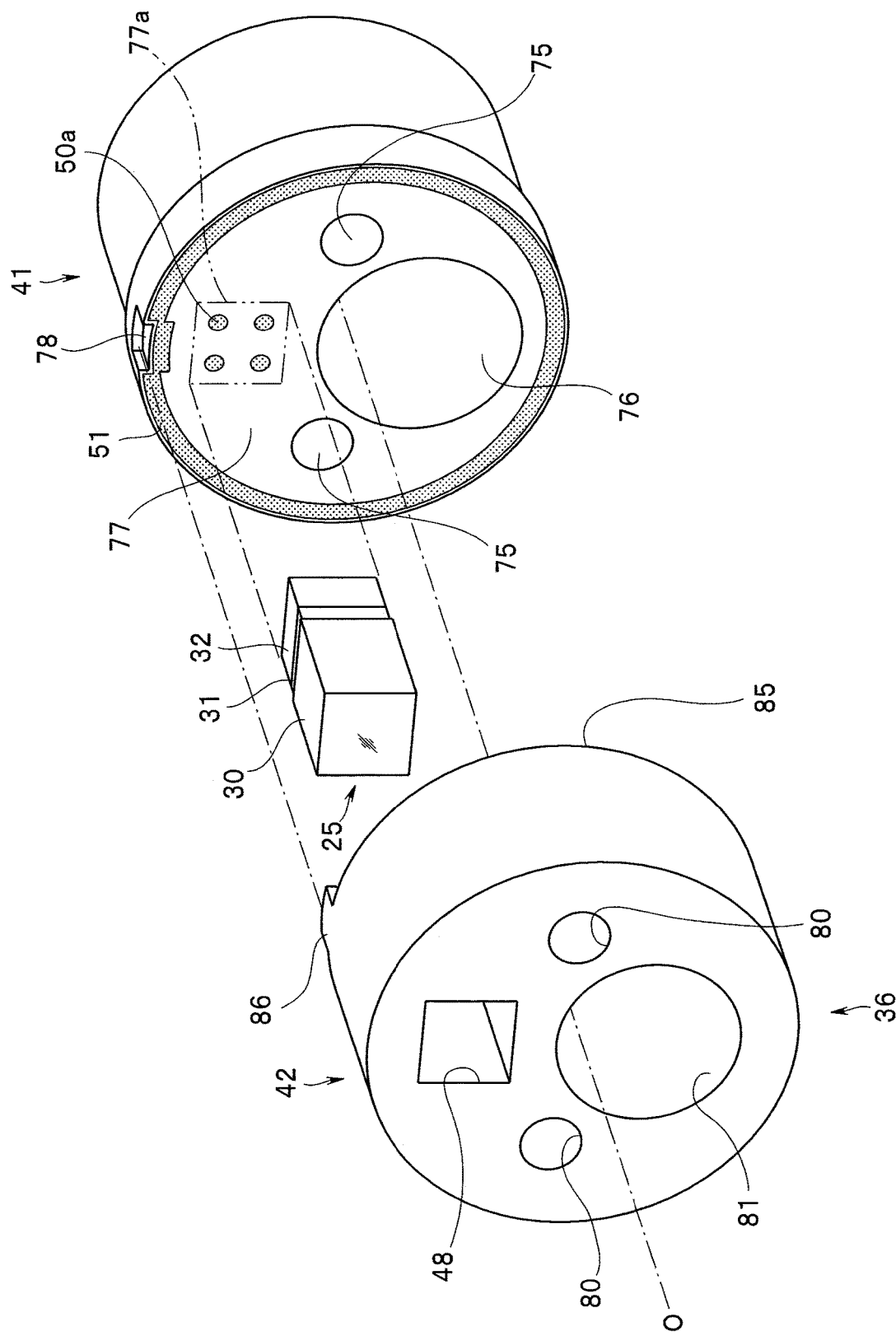
FIG. 17 is a perspective view showing a main part of the distal end unit according to the third embodiment of the present invention, from the distal end side.
Figure 18:
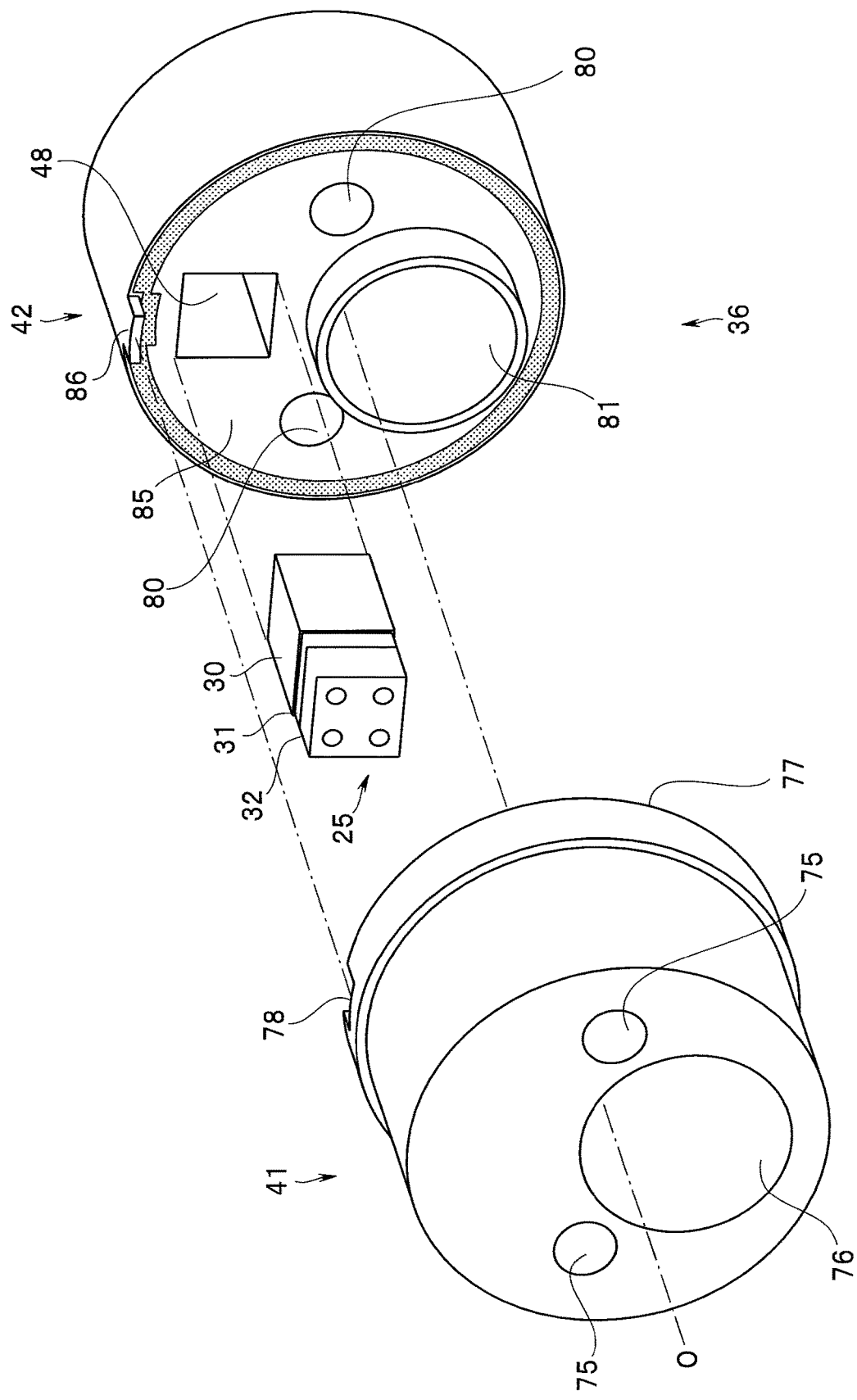
FIG. 18 is a perspective view showing the main part of the distal end unit according to the third embodiment of the present invention, from a proximal end side.

Next, FIG. 16 to FIG. 18 relate to a third embodiment of the present invention; FIG. 16 is a perspective view showing a distal end unit from the distal end side; FIG. 17 is a perspective view showing a main part of the distal end unit from the distal end side; and FIG. 18 is a perspective view showing the main part of the distal end unit from the proximal end side.

Here, in the above first and second embodiments, the configuration has been described in which the distal end frame 36 is divided into two in the direction of the insertion axis O, but the present embodiment is mainly different in that the distal end frame 36 having an approximately cylindrical shape is divided in a direction intersecting with the insertion axis O (for example, direction orthogonal to the insertion axis O). As for other components similar to the first embodiment described above, same signs will be appropriately added and the description will be omitted.

In the present embodiment, a first distal end frame member 41 has an approximately columnar shape. The first distal end frame member 41 is provided with a first light source housing hole portion 75 that is formed of a through hole constituting a light source housing chamber 55, and a first channel housing hole portion 76 that is formed of a through hole constituting a channel holding chamber 56.

The distal end surface of the first distal end frame member 41 is formed as a first joining surface 77 which is a joining surface with a second distal end frame member 42, and a part of the joining surface 77 is set as a mounting surface 77a on which the image pickup unit 25 is mounted. A plurality of connection lands 50a as a first metal pattern are provided on the mounting surface 77a, and the image pickup device 32 of the image pickup unit 25 is joined to each of the connection lands 50a by a material having electroconductivity. Note that each of the connection lands 50a is electrically connected to the proximal end side, for example, via an unillustrated through hole and the like which are provided in the first distal end frame member 41.

Furthermore, a first shield pattern 51 as the first metal pattern is provided on the joining surface 77 of the first distal end frame member 41. The first shield pattern 51 also serves as a metal layer at the time when the first distal end frame member 41 is joined to the second distal end frame member 42 by solder, and is formed in an annular shape along an edge side portion of the first distal end frame member 41. The first shield pattern 51 is electrically connected to the proximal end side, for example, via an unillustrated through hole and the like which are provided in the first distal end frame member 41.

Furthermore, a fitting recess 78 configured to position the first distal end frame member 41 with respect to the second distal end frame member 42 is provided in a side portion of the distal end side of the first distal end frame member 41.

The second distal end frame member 42 has an approximately columnar shape. The second distal end frame member 42 is provided with a second light source housing hole portion 80 that is formed of a through hole constituting the light source housing chamber 55, and a second channel housing hole portion 81 that is formed of a through hole constituting the channel holding chamber 56.

In addition, the second distal end frame member 42 has an image pickup unit housing chamber 48 formed of a through hole having an approximately rectangular cross section, provided at a position corresponding to the mounting surface 77a.

Furthermore, the proximal end surface of the second distal end frame member 42 is formed as a second joining surface 85 which is a joining surface with the first distal end frame member 41, and a second shield pattern 63 as a second metal pattern is provided on the second joining surface 85. The second shield pattern 63 also serves as a metal layer at the time when the second distal end frame member 42 is joined to the first distal end frame member 41 by solder, and is formed in an annular shape along an edge side portion of the second distal end frame member 42.

In addition, a fitting salient 86 configured to position the second distal end frame member 42 and the first distal end frame member 41 by fitting with the fitting recess 78 is provided on a side portion of the proximal end side of the second distal end frame member 42. Note that it is also possible to provide a fitting salient on the first distal end frame member 41 and provide a fitting recess on the second distal end frame member 42.

The first shield pattern 51 formed on the first joining surface 77 and the second shield pattern 63 formed on the second joining surface 85 are joined by solder, and thereby, the first distal end frame member 41 and the second distal end frame member 42 are joined to each other, and constitute the distal end frame 36 that forms the approximately columnar shape as a whole. Note that also in the solder joining between the first distal end frame member 41 and the second distal end frame member 42, it is desirable to use the solder material having a melting point lower than a melting point of a solder material that is used in solder joining for other portions.

Also in such an embodiment, substantially the same action effect as the action effect in the first embodiment described above can be achieved.

Figure 19:
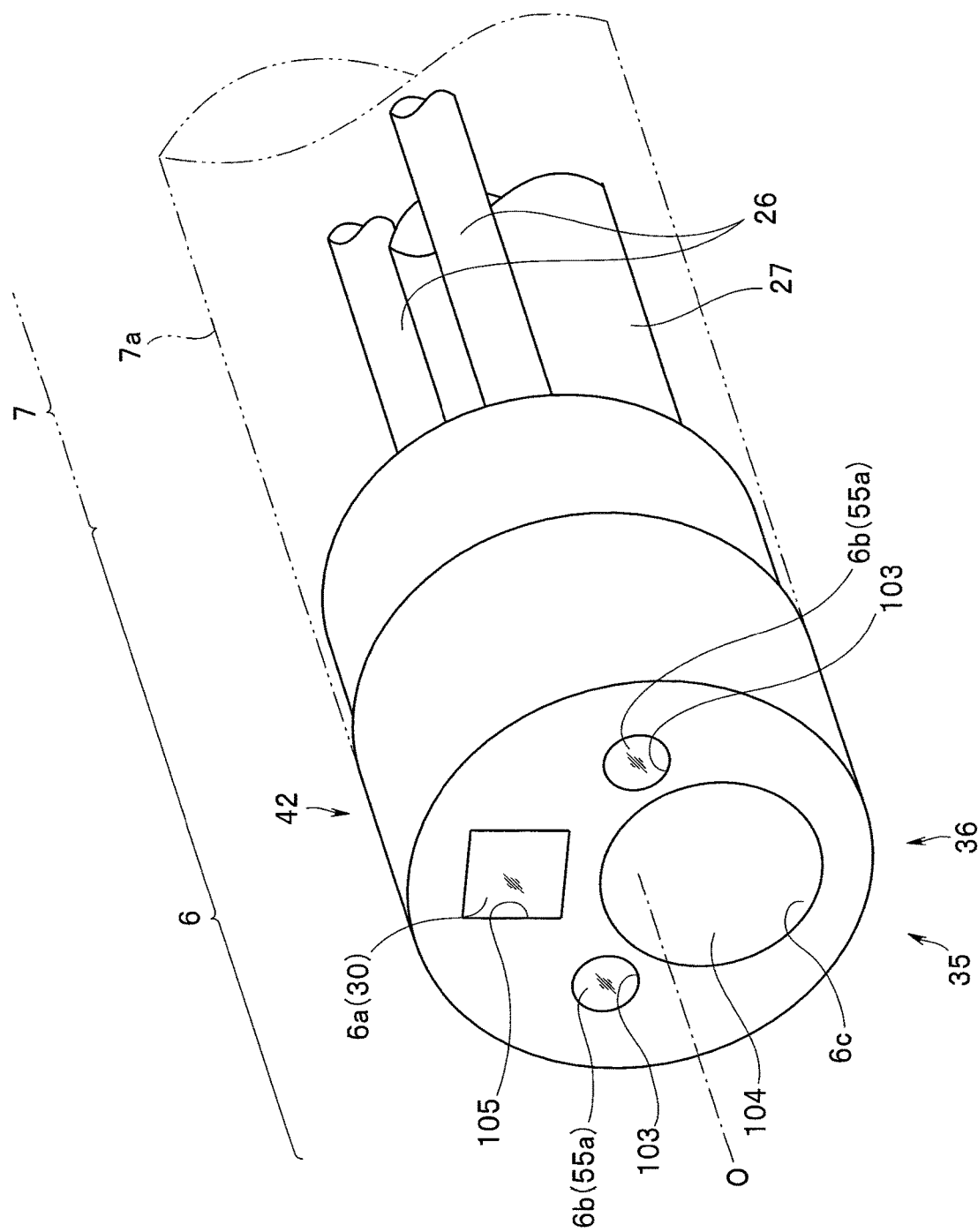
FIG. 19 is a perspective view showing a distal end unit according to a fourth embodiment of the present invention, from a distal end side.
Figure 20:
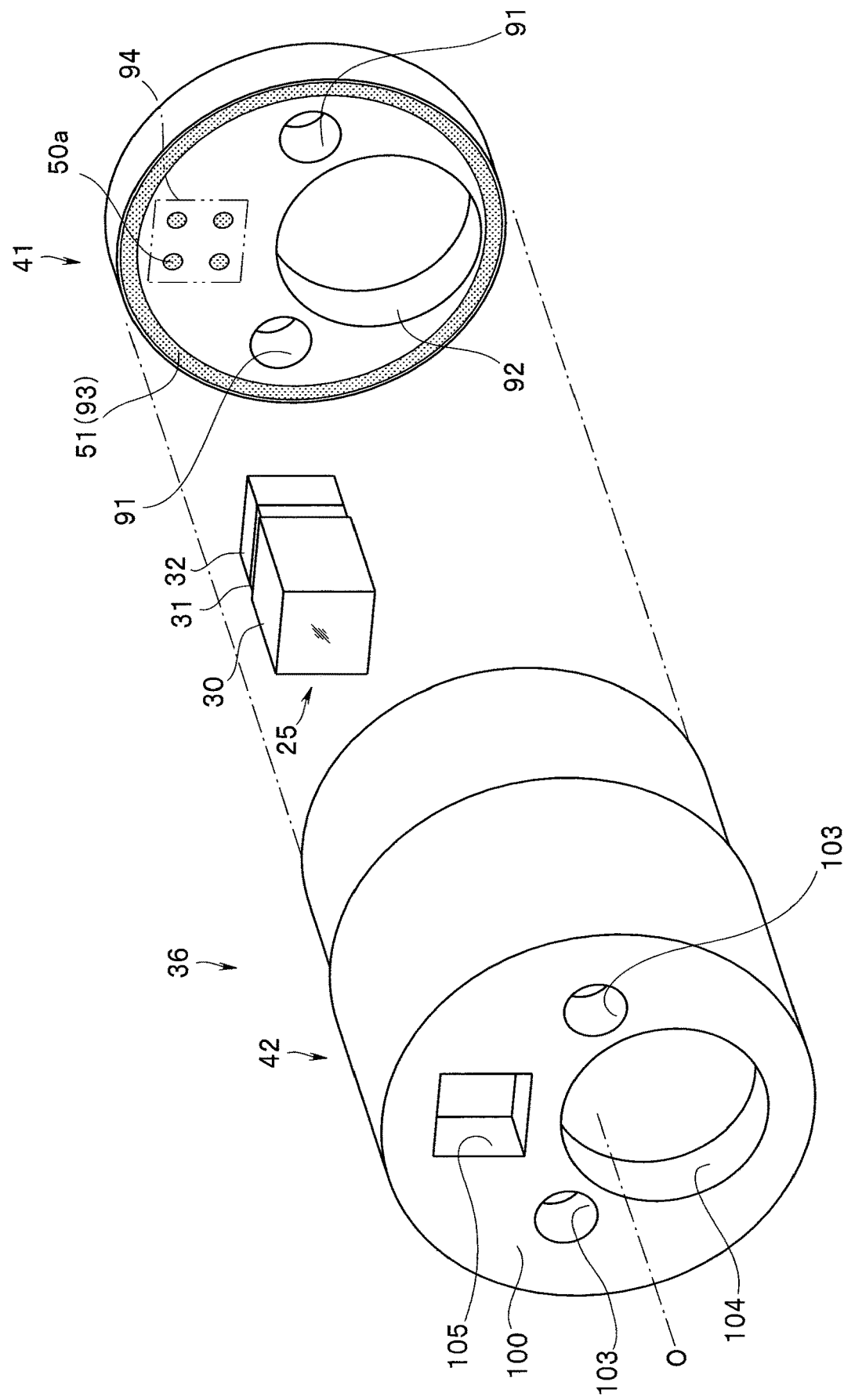
FIG. 20 is an exploded perspective view showing a main part of the distal end unit according to the fourth embodiment of the present invention, from the distal end side.
Figure 21:
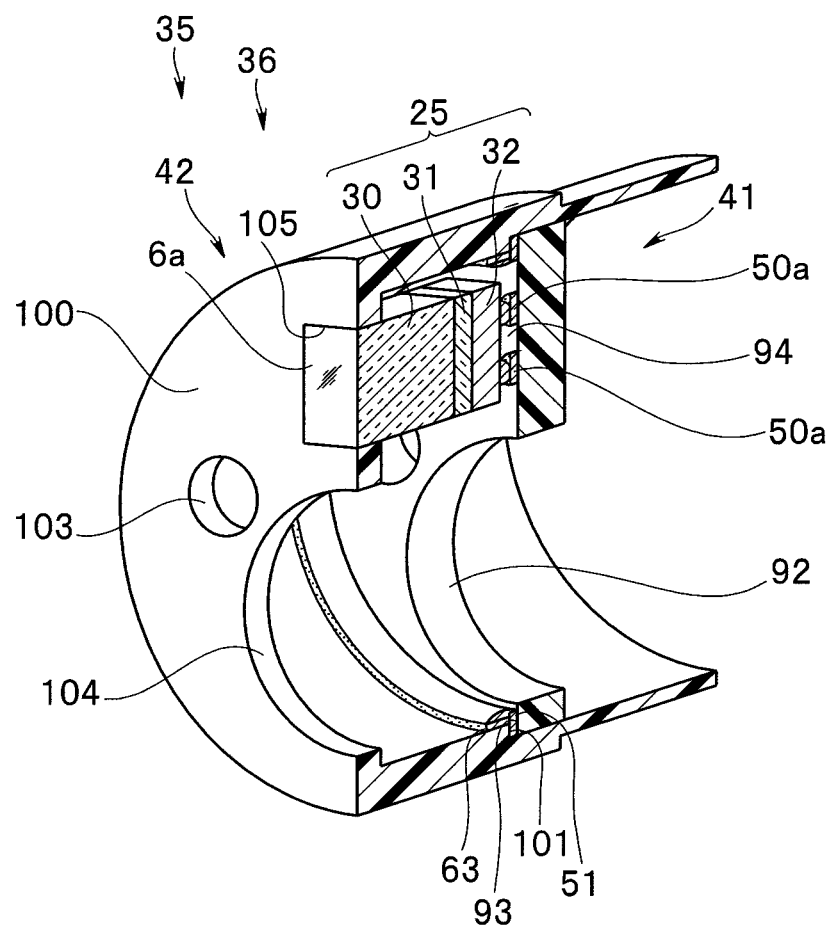
FIG. 21 is a cross-sectional perspective view showing the main part of the distal end unit according to the fourth embodiment of the present invention, from the distal end side.
Figure 22:
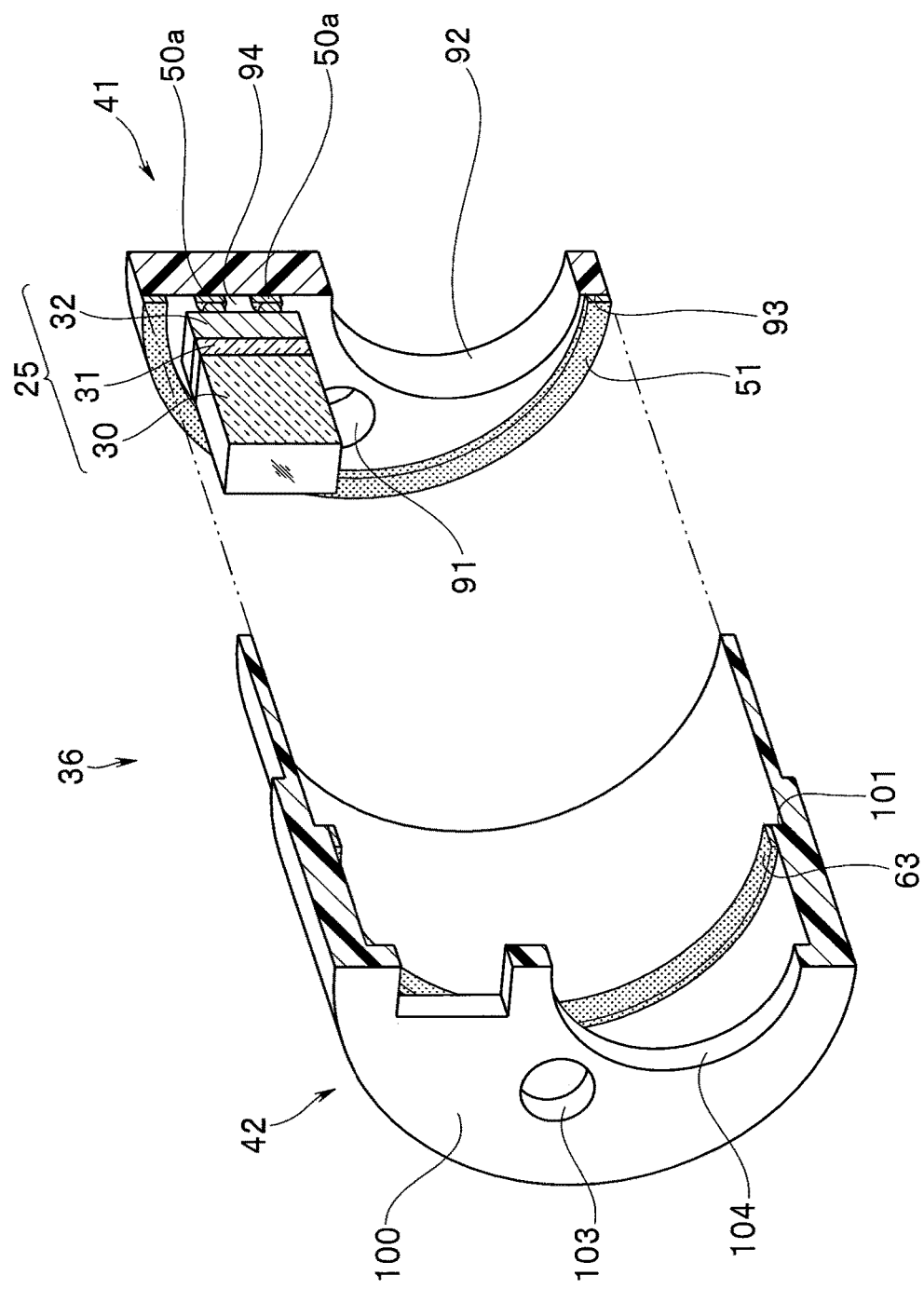
FIG. 22 is an exploded cross-sectional perspective view showing the main part of the distal end unit according to the fourth embodiment of the present invention, from the distal end side.

Next, FIG. 19 to FIG. 22 relate to a fourth embodiment of the present invention; FIG. 19 is a perspective view showing a distal end unit from the distal end side; FIG. 20 is an exploded perspective view showing a main part of the distal end unit from the distal end side; FIG. 21 is a cross-sectional perspective view showing the main part of the distal end unit from the distal end side; and FIG. 22 is an exploded cross-sectional perspective view showing the main part of the distal end unit from the distal end side.

Here, in the above first to third embodiments, the configuration has been described in which the distal end frame 36 is divided into upper and lower portions, left and right portions and the like by the first distal end frame member 41 and the second distal end frame member 42, but the present embodiment is mainly different in that the distal end frame 36 is divided into an inner portion and an outer portion by the first distal end frame member 41 and the second distal end frame member 42. As for other components similar to the first embodiment described above, same signs will be appropriately added and the description will be omitted.

In the present embodiment, the first distal end frame member 41 has an approximately disk shape. The first distal end frame member 41 is provided with first light source holding holes 91 and a first channel holding hole 92 which penetrate in the insertion axis O direction.

In addition, an edge side portion of the distal end surface of the first distal end frame member 41 is set as a first joining surface 93 which is a joining surface with the second distal end frame member 42, and furthermore, a part of an inner region of the distal end surface is set as a mounting surface 94 on which the image pickup unit 25 is mounted.

A plurality of connection lands 50a as a first metal pattern are provided on the mounting surface 94. The image pickup device 32 of the image pickup unit 25 is joined to the connection lands 50a by a material having electroconductivity. Note that each of the connection lands 50a is electrically connected to the proximal end side, for example, via an unillustrated through hole and the like which are provided in the first distal end frame member 41.

Furthermore, a first shield pattern 51 as the first metal pattern is provided on the joining surface 93 of the first distal end frame member 41. The first shield pattern 51 also serves as a metal layer at the time when the first distal end frame member 41 is joined to the second distal end frame member 42 by solder. The first shield pattern 51 is electrically connected to the proximal end side, for example, via an unillustrated through hole and the like which are provided in the first distal end frame member 41.

The second distal end frame member 42 has an approximately cylindrical shape a distal end of which is closed by a front wall 100. An inner diameter of a proximal end of the second distal end frame member 42 is formed to be substantially the same diameter as an outer diameter of the first distal end frame member 41; and furthermore, a stepped portion configured to cause the inner diameter of the distal end side to be smaller than the outer diameter of the first distal end frame member 41 is provided in a middle of an inside of the second distal end frame member 42.

A surface that is formed in the step portion between the two inner peripheral surfaces having different inner diameters is set as a second joining surface 101 which is a joining surface with the first distal end frame member 41.

In addition, a second shield pattern 63 as a second metal pattern is provided in a region adjacent to the second joining surface 101, on an inner peripheral surface of the second distal end frame member 42 the diameter of which has been reduced by the stepped portion.

In addition, the front wall 100 of the second distal end frame member 42 is provided with second light source holding holes 103 and a second channel holding hole 104 which penetrate in the insertion axis O direction, at positions corresponding to the first light source holding holes 91 and the first channel holding hole 92, respectively.

Furthermore, the front wall 100 of the second distal end frame member 42 has an image pickup unit holding hole 105 that penetrates in the insertion axis O direction, provided at a position corresponding to the mounting surface 94.

The first distal end frame member 41 is inserted into an inside of such a second distal end frame member 42, from the proximal end side. The first distal end frame member 41 is positioned with respect to the second distal end frame member 42 in the insertion axis O direction by contact between the first joining surface 93 and the second joining surface 101, and then, the first shield pattern 51 and the second shield pattern 63 are joined to each other by solder. Thereby, the distal end frame 36 is formed that has the approximately columnar shape as a whole.

At the time, a lens unit 30 for image pickup of the image pickup unit 25 that is mounted on the mounting surface 94 is inserted into the image pickup unit holding hole 105, and then is sealed by an adhesive agent or the like. In addition, the light guide 26 is inserted into and held by the first light source holding hole 91 and the second light source holding hole 103; and a treatment instrument channel 27 is inserted into and held by the first channel holding hole 92 and the second channel holding hole 104.

Also in such an embodiment, substantially the same action effect as the action effect in the first embodiment described above can be achieved.

Figure 23:
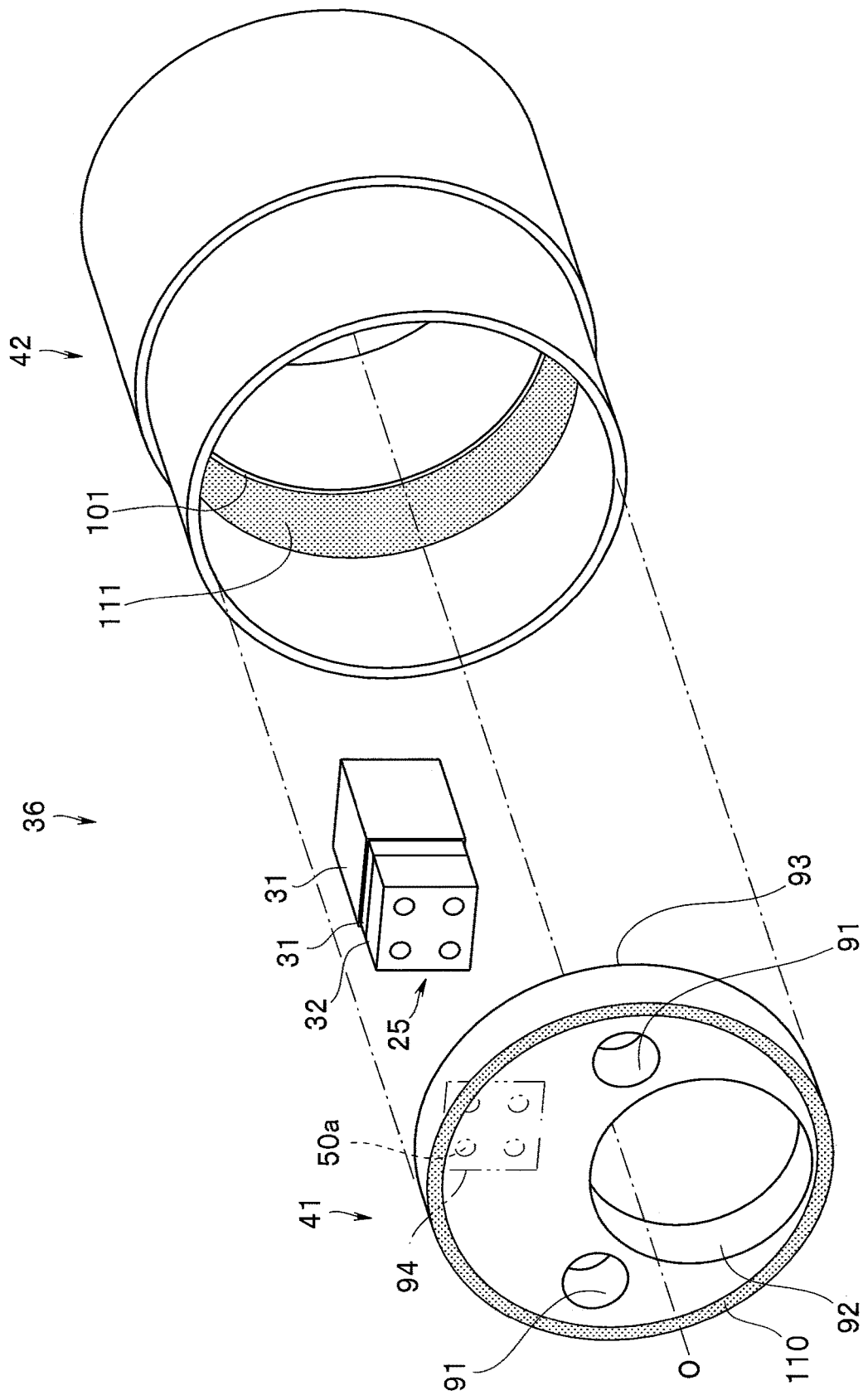
FIG. 23 is an exploded perspective view showing a main part of a distal end unit according to a first modification in the fourth embodiment of the present invention, from a proximal end side.
Figure 24:
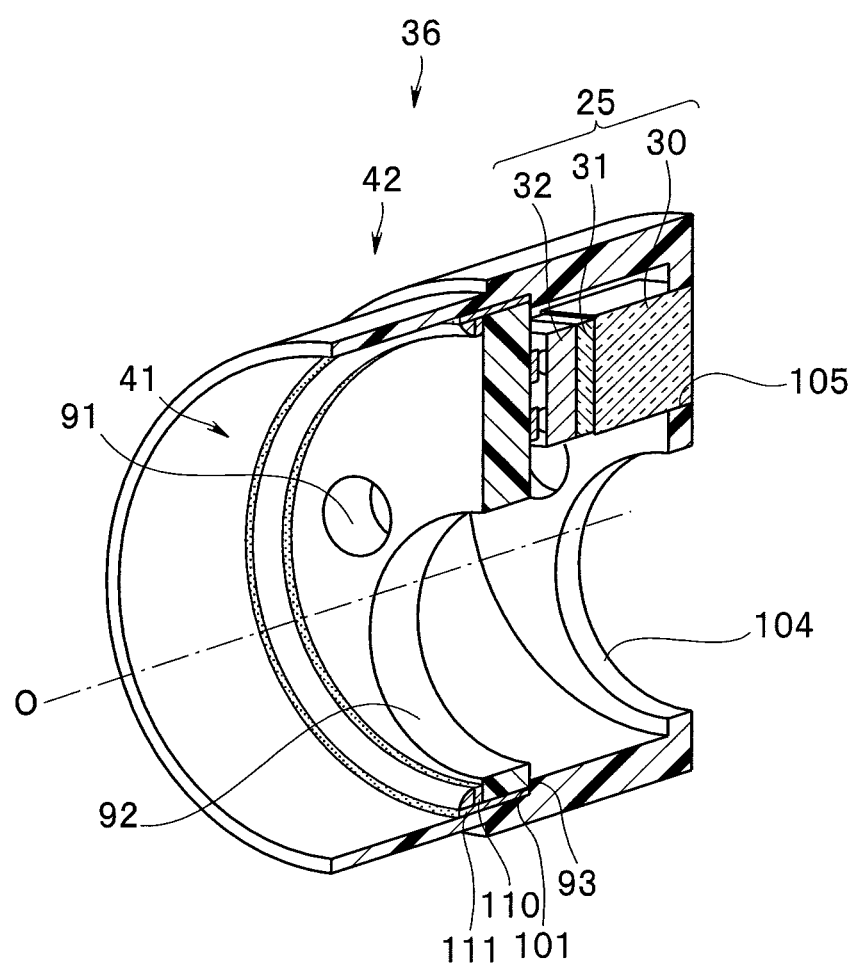
FIG. 24 is a cross-sectional perspective view showing the main part of the distal end unit according to the first modification in the fourth embodiment of the present invention, from the proximal end side.
Figure 25:
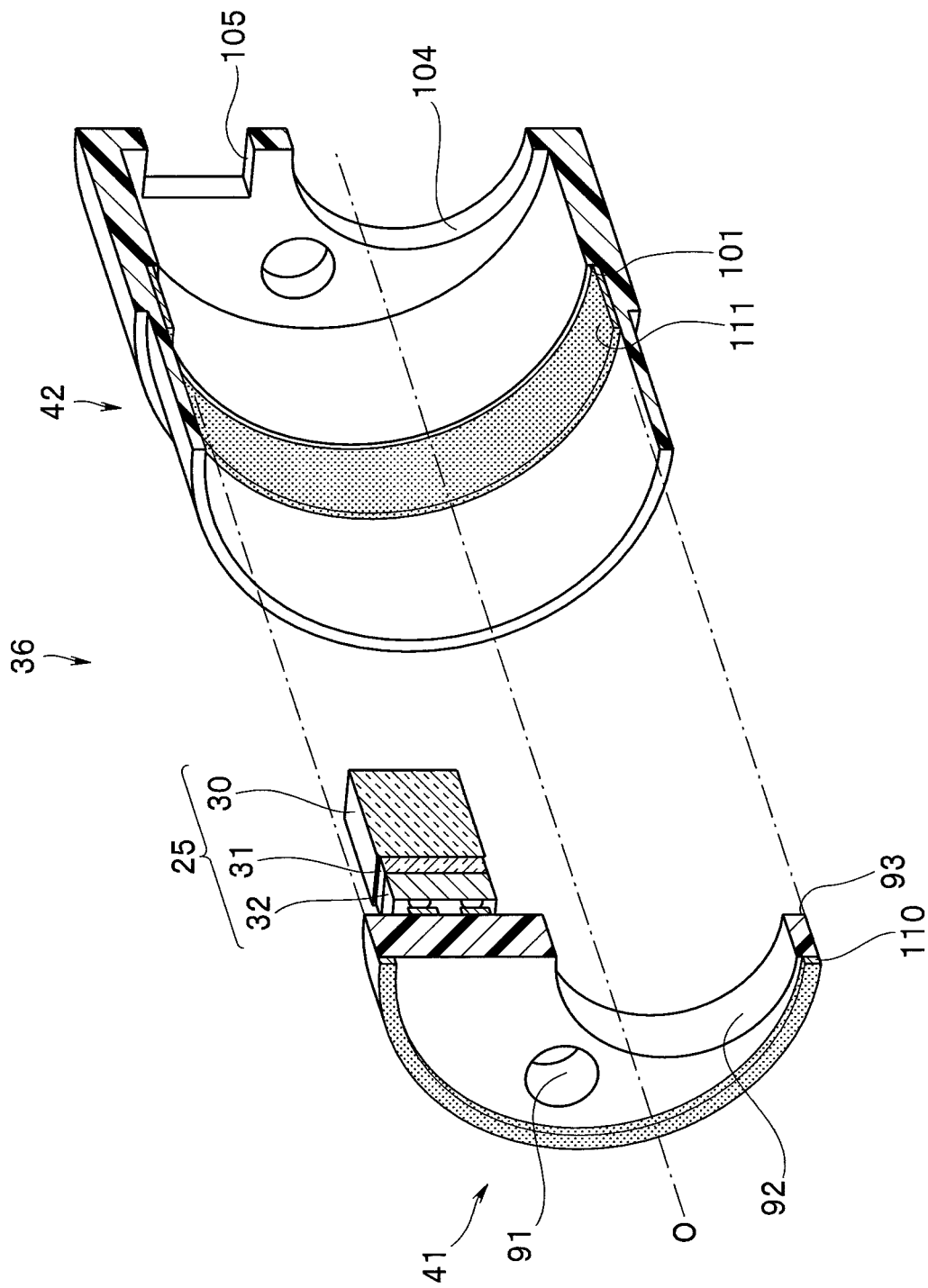
FIG. 25 is an exploded cross-sectional perspective view showing the main part of the distal end unit according to the first modification in the fourth embodiment of the present invention, from the proximal end side.

Here, it is also possible, for example, as shown in FIG. 23 to FIG. 25 to provide a first metal layer 110 for solder connection as the first metal pattern on an edge side portion of the proximal end surface of the first distal end frame member 41; also provide a second metal layer 111 for solder connection as the second metal pattern on an inner peripheral surface of the second distal end frame member 42 on the proximal end side with respect to the second joining surface 101; and join the first metal layer 110 and the second metal layer 111 by solder.

Note that the present invention is not limited to the embodiments described above, and various modifications and changes can be made, which are also within the technical scope of the present invention.

For example, in each of the above embodiments and modifications, an example has been described in which both of the first distal end frame member and the second distal end frame member are composed of the resin molded product which constitutes the molded interconnect device, but, for example, the second distal end frame member can be composed of a product other than the resin molded product which constitutes the molded circuit interconnect device.

In addition, it goes without saying that for example, the configurations of each of the above embodiments and each of the modifications may be appropriately combined.

What is claimed is:

1. A distal end frame of an endoscope, comprising:
a first distal end frame member that comprises a resin molded product which constitutes a molded interconnect device having a metal pattern formed on a surface of the resin molded product;
a housing chamber that is provided on a distal end side of the first distal end frame member, and is formed of a recessed portion a distal end and one side of which are opened;
a second distal end frame member that is joined to the first distal end frame member and closes the one side of the housing chamber;
one or more first metal patterns that are formed of the metal pattern constituting the molded interconnect device and are formed in a region including a joining portion with the second distal end frame member, on a surface of the first distal end frame member; and
a joining member configured to join the first distal end frame member and the second distal end frame member to each other.

2. The distal end frame of the endoscope according to claim 1, further comprising:
a cable connection surface that is set on a notch-shaped step which is provided on a proximal end side of the first distal end frame member, wherein
the first metal patterns are extended from the joining portion with the second distal end frame member on the surface of the first distal end frame member, to the cable connection surface.

3. The distal end frame of the endoscope according to claim 1, wherein each of the first metal patterns comprises a signal pattern that is connected to a connection land provided in the housing chamber.

4. The distal end frame of the endoscope according to claim 1, wherein
the second distal end frame member is formed of the resin molded product that constitutes the molded interconnect device, and
the distal end frame of the endoscope further comprises one or more second metal patterns that are each composed of the metal pattern constituting the molded interconnect device, and that are formed in a region including a joining portion with the first distal end frame member, on a surface of the second distal end frame member.

5. The distal end frame of the endoscope according to claim 4, wherein
the first metal patterns and the second metal patterns comprise a first shield pattern and a second shield pattern which are configured to electromagnetically shield the housing chamber.

6. The distal end frame of the endoscope according to claim 5, wherein
the joining member is a solder, and joins the first distal end frame member and the second distal end frame member to each other, by connecting at least a part of the first shield pattern and at least a part of the second shield pattern by solder.

7. The distal end frame of the endoscope according to claim 1, further comprising:
a recessed portion that is formed in either one of the joining portion of the first distal end frame member with the second distal end frame member, and the joining portion of the second distal end frame member with the first distal end frame member; and
a salient portion that is formed on another of the owing portion of the first distal end frame member with the second distal end frame member, and the joining portion of the second distal end frame member with the first distal end frame member, and is fitted into the recessed portion.

8. The distal end frame of the endoscope according to claim 7, further comprising:
a groove portion configured to absorb an excess of the joining member, in either one of the recessed portion and the salient portion.

9. A distal end unit of an endoscope, comprising:
a distal end frame, and an image pickup unit provided in a housing chamber, wherein
the distal end frame comprises: a first distal end frame member that comprises a resin molded product which constitutes a molded interconnect device having a metal pattern formed on a surface of the resin molded product; the housing chamber that is provided on a distal end side of the first distal end frame member, and is formed of a recessed portion a distal end and one side of which are opened; a second distal end frame member that is joined to the first distal end frame member and closes the one side of the housing chamber; one or more first metal patterns that are formed of the metal pattern constituting the molded interconnect device and are formed in a region including a joining portion with the second distal end frame member, on a surface of the first distal end frame member; and a joining member configured to join the first distal end frame member and the second distal end frame member to each other.

10. An endoscope comprising:
a distal end frame, and an image pickup unit provided in a housing chamber, wherein
the distal end frame comprises: a first distal end frame member that comprises a resin molded product which constitutes a molded interconnect device having a metal pattern formed on a surface of the resin molded product; the housing chamber that is provided on a distal end side of the first distal end frame member, and is formed of a recessed portion a distal end and one side of which are opened; a second distal end frame member that is joined to the first distal end frame member and closes the one side of the housing chamber; one or more first metal patterns that are formed of the metal pattern constituting the molded interconnect device and are formed in a region including a joining portion with the second distal end frame member, on a surface of the first distal end frame member; and a joining member configured to join the first distal end frame member and the second distal end frame member to each other.

* * * * *